(12) United States Patent
Tanaka et al.

(10) Patent No.: US 7,696,347 B2
(45) Date of Patent: Apr. 13, 2010

(54) OXYMETHYL BORON COMPOUNDS

(75) Inventors: Keigo Tanaka, Tsukuba (JP); Satoshi Inoue, Tsukuba (JP); Daisuke Ito, Tsukuba (JP); Norio Murai, Tsukuba (JP); Yosuke Kaburagi, Tsukuba (JP); Shuji Shirotori, Tsukuba (JP); Shuichi Suzuki, Tsukuba (JP); Yoshiaki Ohashi, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 11/886,340

(22) PCT Filed: Mar. 13, 2006

(86) PCT No.: PCT/JP2006/304894

§ 371 (c)(1),
(2), (4) Date: Jun. 2, 2008

(87) PCT Pub. No.: WO2006/098270

PCT Pub. Date: Sep. 21, 2006

(65) Prior Publication Data

US 2008/0242859 A1  Oct. 2, 2008

(30) Foreign Application Priority Data

Mar. 14, 2005  (JP) ............................ 2005-070607
Oct. 7, 2005  (JP) ............................ 2005-294589

(51) Int. Cl.
*C07F 273/04* (2006.01)
(52) U.S. Cl. ..................... 544/69; 544/229; 546/13; 546/8; 548/405; 549/213; 560/125; 560/122
(58) Field of Classification Search .................. None
See application file for complete search history.

(56) References Cited

U.S. PATENT DOCUMENTS

| | | | |
|---|---|---|---|
| 6,858,592 B2 * | 2/2005 | Holmes-Farley et al. | 514/64 |
| 7,049,304 B2 * | 5/2006 | Holmes-Farley et al. | 514/64 |
| 7,456,156 B2 * | 11/2008 | Holmes-Farley et al. | 514/64 |
| 2005/0176988 A1 * | 8/2005 | Khan | 562/7 |

FOREIGN PATENT DOCUMENTS

WO   WO-2003/106384 A   12/2003

OTHER PUBLICATIONS

Gary A. Molander et al., Journal of the American Chemical Society, 2003, vol. 125, No. 37, pp. 11148-11149.
E. Vedejs et al., Journal of Organic Chemistry, 1995, vol. 60, No. 10, pp. 3020-3027.
Masanori Kosugi et al., Chemistry Letters, (1984), pp. 1225-1226.
Masanori Kosugi et al., Chemistry Letters, (1985), pp. 997-998.
Japanese Office Action dated Jul. 29, 2008 regarding Japanese Application No. 2007-508123.

* cited by examiner

*Primary Examiner*—Porfirio Nazario Gonzalez
*Assistant Examiner*—Chukwuma O Nwaonicha
(74) *Attorney, Agent, or Firm*—Birch, Stewart, Kolasch & Birch, LLP.

(57) ABSTRACT

The present invention provides compounds which are useful as safe substitutes for the organotin reagent used in coupling reaction for the oxymethylation of aromatic rings, such as alkoxymethylation or hydroxymethylation, with a palladium catalyst and which can dispense with chromatographic purification with silica gel in the production and are suitable for mass production; and compounds applicable even to the oxymethylation of aromatic ring substrates which do not permit coupling reaction by conventional technique or have low reactivity.

7 Claims, No Drawings

OXYMETHYL BORON COMPOUNDS

This application is a national phase application filed under 35 U.S.C. §371 based on PCT/JP2006/304894, having a filing date of Mar. 13, 2006, and which is herein incorporated by reference in its entirety.

TECHNICAL FIELD

The present invention relates to a boron compound which is useful in a reaction for introducing an oxymethyl group (for example, various alkoxymethyl groups and hydroxymethyl groups) into an aromatic ring. In particular, the present invention relates to a boron compound or a salt or a solvate thereof, which is useful in a reaction for introducing various alkoxymethyl groups, for example, a metal alkoxymethyl trifluoroborate and the like represented by the general formula X—O—$CH_2$—$BF_2F_mM_k$. Furthermore, in the formula, M represents an alkali metal or the like, X represents a $C_{1-6}$ alkyl group optionally having a substituent, or a $C_{3-8}$ cycloclakyl group optionally having a substituent or the like, and m and k each independently represents 0 or 1.

BACKGROUND ART

In a coupling reaction of introducing an oxymethyl group such as an alkoxymethyl group or a hydroxymethyl group into an aromatic ring using a palladium catalyst, it is reported to use an organotin reagent such as an alkoxymethyltin reagent and the like. As the organotin reagent used in the reaction, a methoxymethyl tributyltin reagent disclosed in Non-Patent Document 1, a hydroxymethyl tributyltin reagent disclosed in Non-Patent Document 2 or the like has been reported.

Non-Patent Document 1: Chem. Lett. 1984, 1225.
Non-Patent Document 2: Chem. Lett. 1985, 997.

DISCLOSURE OF THE INVENTION

Problem to be Solved by the Invention

There is a problem that these organotin reagents have toxicity peculiar to a tin reagent. In addition, there is a problem that production of these organotin reagents necessitates purification with chromatography using silica gel in many cases, and is not suitable for industrial large scale production. Apart from, or in addition to these problems, there is also a problem that the substrates to which the tin reagents can be applied are limited since there are aromatic ring substrates for which a coupling reaction does not proceed, and since aromatic ring substrates have a low reactivity in the coupling reaction.

There are similar problems also in hydroxymethylation on an aromatic ring.

On the other hand, application of a boron compound which is capable of introducing an oxymethyl group to a coupling reaction is not known.

In particular, in a coupling reaction of alkoxymethylating or hydroxymethylating an aromatic ring using a palladium catalyst, there needs a compound having excellent safety in place of an olganotin reagent.

Further, there also needs a compound which does not necessitate chromatography purification using silica gel or the like, and is suitable for large scale production, and a process for producing the compound.

Apart from, or in addition to the above problems, there also needs a compound for which a reaction proceeds to an aromatic ring substrate to which a coupling reaction does not proceed in the case of the organotin reagent, and an aromatic ring substrate having a low reactivity such as chlorobenzene.

Further, a compound which is capable of introducing an alkoxymethyl group having various functional groups is also demanded.

Accordingly, an object of the present invention is to solve the above problem.

An object of the present invention is to provide a compound having excellent safety in place of an organotin reagent in a coupling reaction of oxymethylating an aromatic ring using a palladium catalyst.

Further, other than or in addition to the above object, an object of the present invention is to provide a compound which does not necessitate chromatography purification using silica gel or the like in its preparation, and is suitable for large scale production.

More, other than or in addition to the above objects, an object of the present invention is to provide a compound for which a reaction proceeds to an aromatic ring substrate to which a coupling reaction does not proceed in the case of the organotin reagent, and an aromatic ring substrate having a low reactivity such as chlorobenzene.

Further, other than or in addition to the above objects, an object of the present invention is to provide a compound which is capable of introducing an alkoxymethyl group having various functional groups into an aromatic ring group or the like.

Means for Solving Problem

The present inventors have found that the above problems can be solved by a boron compound which is capable of introducing an oxymethyl group into an aromatic ring. That is, the present inventors have found that the above problem can be solved by following inventions.

<1> A boron compound which is capable of introducing an oxymethyl group into an aromatic ring, or a salt or a solvate thereof.

<2> In the above item <1>, the oxymethyl group may be an alkoxymethyl group or a hydroxymethyl group.

<3> In the above item <1> or <2>, the boron compound may be a boric acid derivative.

<4> In any one of the above items <1> to <3>, the boron compound may have following partial structural formula:

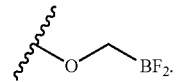

<5> A compound represented by following formula I:

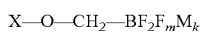

X—O—$CH_2$—$BF_2F_mM_k$ (Formula I), wherein M represents an alkali metal, $N(R^1)(R^2)(R^3)(R^4)$ or $P(R^1)(R^2)(R^3)(R^4)$ in which $R^1$, $R^2$, $R^3$ and $R^4$ each independently represents a $C_{1-6}$ alkyl group or a $C_{7-15}$ aralkyl group;

X represents a $C_{1-6}$ alkyl group optionally having 1 to 3 groups selected from a following group A, a $C_{3-8}$ cycloalkyl group optionally having 1 to 3 groups selected from a following group A, a 5- to 6-membered non-aromatic heterocyclic group optionally having 1 to 3 groups selected from a following group Z, or $R^5C(=O)$ in which $R^5$ represents a hydrogen atom, a $C_{1-6}$ alkyl group or a $C_{3-8}$ cycloalkyl group;

the group A represents an amino group optionally having a $C_{1-6}$ alkyl group or a $C_{3-8}$ cycloalkyl group, a hydroxy group, a $C_{1-6}$ alkyl group, a $C_{3-8}$ cycloalkyl group, a $C_{1-6}$ alkoxy group, a $C_{3-8}$ cycloalkoxy group, and 5- to 6-membered non-aromatic heterocyclic group optionally having 1 to 3 groups selected from the following group Z;

the group Z represents a $C_{1-6}$ alkyl group or a $C_{1-6}$ alkoxycarbonyl group;

m represents an integer of 0 or 1;

k represents an integer of 0 or 1, provided that when m=0, X can form a ring structure together with a boron atom; or a solvate thereof.

<6> A compound represented by following formula I-a:

X—O—CH$_2$—BF$_3$M (Formula I-a), wherein M represents an alkali metal, $N(R^1)(R^2)(R^3)(R^4)$ or $P(R^1)(R^2)(R^3)(R^4)$ in which $R^1$, $R^2$, $R^3$ and $R^4$ each independently represents a $C_{1-6}$ alkyl group or a $C_{7-15}$ aralkyl group, provided that M forms a counterion with an anion in a molecule;

X represents a $C_{1-6}$ alkyl group optionally having 1 to 3 groups selected from a following group A, a $C_{3-8}$ cycloalkyl group optionally having 1 to 3 groups selected from a following group A, a 5- to 6-membered non-aromatic heterocyclic group optionally having 1 to 3 groups selected from a following group Z, or $R^5C(=O)$ in which $R^5$ represents a hydrogen atom, a $C_{1-6}$ alkyl group or a $C_{3-8}$ cycloalkyl group;

the group A represents an amino group optionally having a $C_{1-6}$ alkyl group or a $C_{3-8}$ cycloalkyl group, a hydroxy group, a $C_{1-6}$ alkyl group, a $C_{3-8}$ cycloalkyl group, a $C_{1-6}$ alkoxy group, a $C_{3-8}$ cycloalkoxy group, and 5- to 6-membered non-aromatic heterocyclic group optionally having 1 to 3 groups selected from a following group Z;

the group Z represents a $C_{1-6}$ alkyl group or a $C_{1-6}$ alkoxycarbonyl group;

a compound represented by following formula II, wherein the definition of X is the same as defined above:

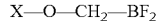
X—O—CH$_2$—BF$_2$ (Formula II);

or a compound represented by following formula III, wherein the definition of M is the same as defined above, and n represents an integer of 2 or 3:

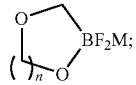
(III)

or a solvate thereof.

<7> In the above item <5> or <6>, M may be an alkali metal.

<8> In any one of the above items <5> to <7>, M may be potassium or sodium.

<9> In any one of the above items <5> to <8>, the 5- to 6-membered non-aromatic heterocyclic group may be a tetrahydrofuranyl group, a tetrahydropyranyl group, a piperidyl group, a pyrrolidinyl group or a morpholinyl group.

<10> In any one of the above items <5> to <9>, X may be a $C_{1-6}$ alkyl group optionally having 1 to 3 groups selected from a following group A1;

the group A1 represents an amino group optionally having a $C_{1-6}$ alkyl group or a $C_{3-8}$ cycloalkyl group, a hydroxy group, a $C_{1-6}$ alkyl group, a $C_{3-8}$ cycloalkyl group, a $C_{1-6}$ alkoxy group, a $C_{3-8}$ cycloalkoxy group, and a 5- to 6-membered non-aromatic heterocyclic group optionally having 1 to 3 groups selected from a following group Z1;

the group Z1 represents a $C_{1-6}$ alkyl group or a $C_{1-6}$ alkoxycarbonyl group.

<11> A compound selected from a group consisting of potassium t-butoxymethyl trifluoroborate, potassium methoxymethyl trifluoroborate, potassium ethoxymethyl trifluoroborate, potassium (2-methoxyethoxymethyl) trifluoroborate, potassium cyclopropylmethoxymethyl trifluoroborate, potassium {[2-(dimethylamino)ethoxy]methyl} trifluoroborate, potassium cyclobutoxymethyl trifluoroborate, potassium 2-piperidin-1-ylethoxy-methyl trifluoroborate, potassium [(2-morpholine-4-ylethoxy)methyl]trifluoroborate, potassium trifluoro[(3-morpholin-4-ylpropoxy)methyl]borate, potassium (1-methyl-piperidin-4-yloxy)-methyl trifluoroborate, tetrabutylammonium methoxymethyl trifluoroborate, potassium {[2-(1-methylpiperazin-4-yl)ethoxy]methyl} trifluoroborate, potassium 4-(dimethylamino)butoxymethyl trifluoroborate, potassium {2-[cyclohexyl(methyl)amino]ethoxy}methyl trifluoroborate, (2-methylpropoxy)methyl boronic acid, sodium cyclopropylmethoxymethyl trifluoroborate, potassium butoxymethyl trifluoroborate, sodium [[[[3R]-1-t-butoxycarbonyl]pyrrolidin-3-yl]oxy]methyl (trifluoro)borate, sodium isopropoxymethyl trifluoroborate, sodium tetrahydrofuran-2-ylmethoxymethyl trifluoroborate, sodium tetrahydropyran-4-yloxy-methyl trifluoroborate, sodium 2-cyclohexyloxy-ethoxymethyl trifluoroborate, sodium 3-methoxy-1-propoxymethyl trifluoroborate, sodium (2-hydroxyethoxy)methyl trifluoroborate, potassium acetoxymethyl trifluoroborate, sodium formyloxymethyl trifluoroborate, sodium [(cyclopentylcarbonyl)oxy]methyl trifluoroborate, and sodium [(2,2-dimethyl)propionyloxy]methyl trifluoroborate; or a solvate thereof.

<P1> A compound represented by following formula $I_p$:

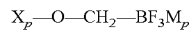
$X_p$—O—CH$_2$—BF$_3$M$_p$ (Formula $I_p$), wherein M represents an alkali metal;

$X_p$ represents a $C_{1-6}$ alkyl group optionally having 1 to 3 groups selected from a following group $A_p$, a $C_{3-8}$ cycloalkyl group optionally having 1 to 3 groups selected from a following group $A_p$, a pyrrolidin-3-yl group optionally having 1 to 3 groups selected from a following group $Z_p$, a piperidin-3-yl group optionally having 1 to 3 groups selected from a following group $Z_p$, a piperidin-4-yl group optionally having 1 to 3 groups selected from a following group $Z_p$, a tetrahydrofuran-3-yl group or a tetrahydrofuran-4-yl group; or a solvate thereof.

The group $A_p$ represents the group consisting of a $C_{1-6}$ alkyl group, a $C_{3-8}$ cycloalkyl group optionally having 1 to 3 groups selected from a following group $Z_p$, a $C_{1-6}$ alkoxy group, a $C_{3-8}$ cycloalkyloxy group, a tetrahydrofuran-2-yl group, a tetrahydrofuran-3-yl group, a tetrahydropyran-2-yl group, a tetrahydropyran-3-yl group, a tetrahydropyran-4-yl group, a pyrrolidin-2-yl group optionally having 1 to 3 groups selected from a following group $Z_p$, a pyrrolidin-3-yl group optionally having 1 to 3 groups selected from a following group $Z_p$, a piperidin-2-yl group optionally having 1 to 3 groups selected from a following group $Z_p$, a piperidin-3-yl group optionally having 1 to 3 groups selected from a following group $Z_p$, a piperidin-4-yl group optionally having 1 to 3 groups selected from a following group $Z_p$, a morpholin-2-yl group optionally having 1 to 3 groups selected from a following group $Z_p$, a morpholin-3-yl group optionally having 1 to 3 groups selected from a following group $Z_p$, a piperazin-2-yl group optionally having 1 to 3 groups selected from a following group $Z_p$, and a group represented by the formula —$X_p^2$—$X_p^3$ (wherein $X_p^2$ represents a methylene group optionally having 1 to 2 groups selected from a following group $Z_p$, $X_p^3$ represents a group represented by the formula —NR$_p^2$R$_p^3$ (wherein R$_p^2$ and R$_p^3$ each independently represents a hydrogen atom, a C$_{1-6}$ alkyl group or a C$_{3-8}$ cycloalkyl group), a hydroxy group, an azetidin-1-yl group, a pyrrolidin-1-yl group, a piperidin-1-yl group, an azepan-1-yl group, an azokan-1-yl group, a morpholin-4-yl group, a thiomorpholin-4-yl group or a piperazin-1-yl group optionally having one group selected from a following group Z$_p$).

The group B$_p$ represents a C$_{1-6}$ alkyl group.

<P2> In the above item <P1>, M$_p$ may be potassium or sodium.

<P3> In the above item <P1>, M$_p$ may be potassium.

<P4> In any one of the above items <P1> to <P3>, X$_p$ may be a C$_{1-6}$ alkyl group optionally having 1 to 3 groups selected from a following group A$_p$2. The group A$_p$2 represents a group consisting of a 2-dimethylaminoethyl group, a 2-methoxyethyl group, and a cyclopropylmethyl group.

<P5> In any one of the above items <P1> to <P3>, X$_p$ may be a C$_{1-6}$ alkyl group, an ethyl group having one group selected from the above-described group A$_p$2, or a methyl group having one group selected from the above-described group A$_p$2.

<P6> In any one of the above items <P1> to <P3>, X$_p$ may be a cyclopropylmethyl group, a t-butyl group, a methyl group, a 2-dimethylaminoethyl group or a 2-methoxyethyl group.

<P7> Use of a compound or a solvate thereof described in any one of the above items <P1> to <P6> as a coupling reagent for a coupling reaction in which an aromatic ring is alkoxymethylated.

<P8> A coupling reagent represented by the above-described formula I$_p$, which alkoxymethylates an aromatic ring by using a palladium catalyst.

<P9> In the above item <P8>, the coupling reagent may have any one of characteristics described in any one of the above items <P1> to <P6>.

Effects of the Invention

The present invention can solve the above-described problem.

The present invention can provide a compound excellent in safety in place of an organotin reagent in a coupling reaction of oxymethylating an aromatic ring using a palladium catalyst.

Further, other than or in addition to the above effects, the present invention can provide a compound which does not necessitate chromatography purification using silica gel or the like in its preparation, and is suitable for large scale production.

Therefore, the compound according to the present invention is also useful as a reaction reagent for introducing an oxymethyl group into an aromatic ring.

More, other than or in addition to the above effects, the present invention can provide a compound for which a reaction proceeds to an aromatic ring substrate to which a coupling reaction does not proceed in the case of the organotin reagent, and an aromatic ring substrate having a low reactivity such as chlorobenzene.

Further, other than or in addition to the above effects, the present invention can provide a compound which is capable of introducing an alkoxymethyl group having various functional groups into an aromatic ring group or the like.

Preferred Embodiments for Carrying Out the Present Invention

The present invention will be described in detail hereinafter.

The present invention provides a boron compound which is capable of introducing an oxymethyl group into an aromatic ring, or a salt or a solvate thereof.

Hereinafter, various terms used herein will be described.

The term "aromatic ring" used herein means a cyclic compound having aromaticity, may be monocyclic or dicyclic, may be an aromatic hydrocarbon cyclic group or an aromatic heterocyclic group, may have a substituent. Examples may include a benzene ring, naphthalene ring, furan ring, thiophene ring, pyrrole ring, imidazole ring, triazole ring, tetrazole ring, thiazole ring, pyrazole ring, oxazole ring, isoxazole ring, isothiazole ring, furazan ring, thiadiazole ring, oxadiazole ring, pyridine ring, pyrazine ring, pyridazine ring, pyrimidine ring, triazine ring, purinyl ring, pteridine ring, quinoline ring, isoquinoline ring, naphthyridine ring, quinoxaline ring, cinnoline ring, quinazoline ring, phthalazine ring, imidazopyridine ring, imidazothiazole ring, imidazooxazole ring, benzothiazole ring, benzoxazole ring, benzimidazole ring, indole ring, isoindole ring, indazole ring, pyrrolopyridine ring, thienopyridine ring, furopyridine ring, benzothiadiazole ring, benzoxadiazole ring, pyridpyrimidine ring, benzofuran ring, benzothiophene ring, benzo[1,3]dioxole ring, thienofuran ring or the like.

The term "oxymethyl group" used herein means an alkoxymethyl group or a hydroxymethyl group, and may include a group which is converted into a hydroxymethyl group by predetermined treatment such as hydrolysis and the like.

The term "boron compound" used herein represents a compound having a boron atom in its structure, for example, represents a boronic acid derivative represented by following formula (IV) or formula (V):

$$\text{XO—CH}_2\text{—B(OH)}_2 \qquad \text{(Formula IV)},$$

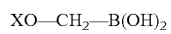

wherein X represents a C$_{1-6}$ alkyl group optionally having 1 to 3 groups selected from a following group A, a C$_{3-8}$ cycloalkyl group optionally having 1 to 3 groups selected from a following group A, a 5- to 6-membered non-aromatic heterocyclic group optionally having 1 to 3 groups selected from a following Z group, or R$^5$C(=O) (wherein R$^5$ represents a hydrogen atom, a C$_{1-6}$ alkyl group or a C$_{3-8}$ cycloalkyl group);

the group A represents an amino group optionally having a C$_{1-6}$ alkyl group or a C$_{3-8}$ cycloalkyl group, a hydroxy group, a C$_{1-6}$ alkyl group, a C$_{3-8}$ cycloalkyl group, a C$_{1-6}$ alkoxy group, a C$_{3-8}$ cycloalkoxy group, and a 5- to 6-membered non-aromatic heterocyclic group optionally having 1 to 3 groups selected from a following group Z;

the group Z represents a C$_{1-6}$ alkyl group or a C$_{1-6}$ alkoxycarbonyl group, a compound represented by following partial structural formula or a compound represented by following formula I, and is preferably a compound represented by the formula I.

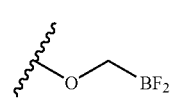

X—O—CH$_2$—BX$_2$F$_m$M$_k$. (Formula I)

wherein M represents an alkali metal, $N(R^1)(R^2)(R^3)(R^4)$ or $P(R^1)(R^2)(R^3)(R^4)$ (wherein $R^1$, $R^2$, $R^3$ and $R^4$ each independently represents a $C_{1-6}$ alkyl group or a $C_{7-15}$ aralkyl group), provided that M forms a counterion with an anion in a molecule;

X represents a $C_{1-6}$ alkyl group optionally having 1 to 3 groups optionally having 1 to 3 groups selected from a following group A, a $C_{3-8}$ cycloalkyl group optionally having 1 to 3 groups selected from a following group A, a 5- to 6-membered non-aromatic heterocyclic group optionally having 1 to 3 groups selected from a following group Z, or $R^5C(=O)$ (wherein $R^5$ represents a hydrogen atom, a $C_{1-6}$ alkyl group or a $C_{3-8}$ cycloalkyl group);

the group A represents an amino group optionally having a $C_{1-6}$ alkyl group or a $C_{3-8}$ cycloalkyl group, a hydroxyl group, a $C_{1-6}$ alkyl group, a $C_{3-8}$ cycloalkyl group, a $C_{1-6}$ alkoxy group, a $C_{3-8}$ cycloalkoxy group, and a 5- to 6-membered non-aromatic heterocyclic group optionally having 1 to 3 groups selected from a following group Z;

the group Z represents a $C_{1-6}$ alkyl group or a $C_{1-6}$ alkoxycarbonyl group;

m represents an integer of 0 or 1; and k represents an integer of 0 or 1, provided that when m=0, X can form a ring structure together with a boron atom.

Preferably, X may be a $C_{1-6}$ alkyl group optionally having 1 to 3 groups selected from the following group A, or $R^5C(=O)$ (wherein $R^5$ represents a hydrogen atom, a $C_{1-6}$ alkyl group or a $C_{3-8}$ cycloalkyl group).

The group A represents an amino group optionally having a $C_{1-6}$ alkyl group or a $C_{3-8}$ cycloalkyl group, a hydroxy group, a $C_{1-6}$ alkyl group, a $C_{3-8}$ cycloalkyl group, a $C_{1-6}$ alkoxy group, a $C_{3-8}$ cycloalkoxy group, and a 5- to 6-membered non-aromatic heterocyclic group optionally having 1 to 3 groups selected from the following group Z. It is preferable that the 5- to 6-membered non-aromatic heterocyclic group may be a tetrahydrofuranyl group, a tetrahydropyranyl group, a piperidyl group, a pyrrolidinyl group or a morpholinyl group.

The group Z represents a $C_{1-6}$ alkyl group or a $C_{1-6}$ alkoxycarbonyl group. Methyl group or t-butyloxycarbonyl group is preferable.

Also, the present invention provides a compound represented by the formula I-a, a compound represented by formula II, or a boron compound represented by formula III. In the formulae I-a, and III, the definition of M is the same as defined above. In the formulae I-a, II and III, the definition of X is the same as defined above. Preferable is a compound represented by the formula I-a.

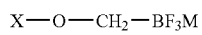

(Formula I-a)

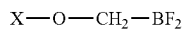

(Formula II)

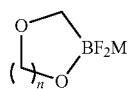

III

In the present application, the "alkali metal" refers to a metal belonging to Periodic Table Group 1, and examples include lithium, sodium and potassium.

The term "$C_{1-6}$ alkyl group" used herein means linear or branched alkyl group having 1 to 6 carbon atoms, which is a monovalent group derived by removing one arbitrary hydrogen atom from an aliphatic hydrocarbon having 1 to 6 carbon atoms. Specifically, examples may include a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, a 2,3-dimethyl-2-butyl group and the like.

The term "$C_{3-8}$ cycloalkyl group" used herein represents a cyclic aliphatic hydrocarbon group having 3 to 8 carbon atoms. The examples may include a cyclopropyl group, a cyclobutyl group, a cyclopentyl group, a cyclohexyl group, a cycloheptyl group, a cyclooctyl group, and the like.

The term "$C_{1-6}$ alkoxy group" used herein represents an oxy group to which the above "$C_{1-6}$ alkyl group" is bound. Specifically, examples may include a methoxy group, an ethoxy group, a 1-propyloxy group, a 2-propyloxy group, a 2-methyl-1-propyloxy group, a 2-methyl-2-propyloxy group, 1-butyloxy group, 2-butyloxy group, 1-pentyloxy group, 2-pentyloxy group, 3-pentyloxy group and the like.

The term "$C_{3-8}$ cycloalkyloxy group" used herein represents an oxy group to which the above defined "$C_{3-8}$ cycloalkyl group" is bound. Specifically, examples may include a cyclopropyloxy group, a cyclobutyloxy group, a cyclopentyloxy group, a cyclohexyloxy group, a cycloheptyloxy group, a cyclooctyloxy group and the like.

The term "$C_{1-6}$ alkoxycarbonyl group" used herein represents a carbonyl group to which the above-defined "$C_{1-6}$ alkoxy group" is bound. Specifically, examples may include a methoxycarbonyl group, an ethoxycarbonyl group, a 1-propyloxycarbonyl group, a 2-propyloxycarbonyl group and the like.

The term "5- to 6-membered non-aromatic heterocyclic group" used herein represents a non-aromatic cyclic group which i) has 5 or 6 atoms which constitute the ring of the cyclic group, ii) contains 1 to 2 heteroatoms in the atoms which constitute the ring, iii) may contain 1 to 2 double bonds in the ring, iv) may contain 1 to 3 carbonyl groups in the ring, and v) is monocyclic. Specifically, examples may include a pyrrolidinyl group, a piperidinyl group, a piperazinyl group, a morpholinyl group, a thiomorpholinyl group, a tetrahydrofuryl group, a tetrahydropyranyl group, a dioxanyl group, a tetrahydrothienyl group, a tetrahydrothiopyranyl group, an oxazolidinyl group, a thiazolidinyl group and the like.

The term "$C_{7-15}$ aralkyl group" used herein represents a functional group in which $C_{6-14}$ aryl group (which represents an aromatic hydrocarbon cyclic group having 6 to 14 carbon atoms. Specifically, the examples may includes a phenyl group, a naphthyl group (1-naphthyl group, 2-naphthyl group), an indenyl group, an azulenyl group, a heptalenyl group, an indacenyl group, a biphenylenyl group, an acenaphthylenyl group, a fluorenyl group, a phenalenyl group, a phenanthrenyl group, an anthracenyl group and the like) is bound to the above "$C_{1-6}$ alkyl group". Specifically, examples may include a benzyl group, an α-naphthylmethyl group, a β-naphthylmethyl group, an indenylmethyl group, a 1-phenethyl group, a 2-phenethyl group, a 1-naphthylethyl group, a 2-naphthylethyl group, a 1-phenylpropyl group, a 2-phenylpropyl group, a 3-phenylpropyl group, a 1-naphthylpropyl group, a 2-naphthylpropyl group, a 3-naphthylpropyl group, a 1-phenylbutyl group, a 2-phenylbutyl group, a 3-phenylbutyl group, a 4-phenylbutyl group, a 1-naphthylbutyl group, a 2-naphthylbutyl group, a 3-naphthylbutyl group, a 4-naphthylbutyl group, a 1-phenylpentyl group, a 2-phenylpentyl group, a 3-phenylpentyl group, a 4-phenylpentyl group, a 5-phenylpentyl group, a 1-naphthylpentyl group, a 2-naphthylpentyl group, a 3-naphthylpentyl group, a 4-naphthylpentyl group, a 5-naphthylpentyl group, a 1-phenylhexyl group, a 2-phenylhexyl group, a 3-phenylhexyl group, a 4-phenylhexyl group, a 5-phenylhexyl group, a 6-phenylhexyl group, a 1-naphthylhexyl group, a 2-naphthylhexyl group, a 3-naphthylhexyl group, a 4-naphthylhexyl group, a 5-naphthylhexyl group, a 6-naphthylhexyl group and the like.

The term "solvate" used herein is a solvate which is formed by the compound of the present invention and a solvent. A kind of the solvent in the solvate, a ratio of the solvent relative to the compound in the solvate, and the like are not particularly limited.

The solvate may preferably be a solvate, an alcoholate (e.g. methanolate, ethanolate, propanolate, isopropanolate and the like), esterate (ethylate acetate and the like), etherate (methyletherate, ethyletherate, tetrahydrofuran and the like), or dimethylformamidate or the like, particularly preferably hydrate, or alcholate (e.g. methanolate, ethanolate). A pharmacologically acceptable solvent is preferable.

Also, in one embodiment, the present invention provides a compound represented by the following formula $I_p$ or a solvate thereof.

$$X_p—O—CH_2—BF_3M_p \qquad \text{Formula } I_p$$

In the formula, $M_p$ represents an alkali metal. $M_p$ may preferably be potassium or sodium, more preferably potassium.

In addition, in the formula, $X_p$ represents a $C_{1-6}$ alkyl group optionally having 1 to 3 groups selected from a following group $A_p$, a $C_{3-8}$ cycloalkyl group optionally having 1 to 3 groups selected from a following group $A_p$, a pyrrolidin-3-yl group optionally having 1 to 3 groups selected from a following group $Z_p$, a piperidin-3-yl group optionally having 1 to 3 groups selected from a following group $Z_p$, piperidin-4-yl group optionally having 1 to 3 groups selected from a following group $Z_p$, a tetrahydrofuran-3-yl group or a tetrahydrofuran-4-yl group.

The group $A_p$ represents the group consisting of a $C_{1-6}$ alkyl group, a $C_{3-8}$ cycloalkyl group optionally having 1 to 3 groups selected from a following group $Z_p$, a $C_{1-6}$ alkoxy group, a $C_{3-8}$ cycloalkyloxy group, a tetrahydrofuran-2-yl group, a tetrahydrofuran-3-yl group, a tetrahydropyran-2-yl group, a tetrahydropyran-3-yl group, a tetrahydropyran-4-yl group, a pyrrolidin-2-yl group optionally having 1 to 3 groups selected from a following group $Z_p$, a pyrrolidin-3-yl group optionally having 1 to 3 groups selected from a following group $Z_p$, a piperidin-2-yl group optionally having 1 to 3 groups selected from a following group $Z_p$, a piperidin-3-yl group optionally having 1 to 3 groups selected from a following group $Z_p$, a piperidin-4-yl group optionally having 1 to 3 groups selected from a following group $Z_p$, a morpholin-2-yl group optionally having 1 to 3 groups selected from a following group $Z_p$, a morpholin-3-yl group optionally having 1 to 3 groups selected from a following group $Z_p$, a piperazin-2-yl group optionally having 1 to 3 groups selected from a following group $Z_p$, and a group represented by the formula —$X_p^2 X_p^3$ (wherein $X_p^2$ represents a methylene group optionally having 1 to 2 groups selected from a following group $Z_p$, $X_p^3$ represents a group represented by the formula —$NR_p^2 R_p^3$ (wherein $R_p^2$ and $R_p^3$ each independently represents a hydrogen atom, a $C_{1-6}$ alkyl group or a $C_{3-8}$ cycloalkyl group), a hydroxy group, an azetidin-1-yl group, a pyrrolidin-1-yl group, a piperidin-1-yl group, an azepan-1-yl group, an azokan-1-yl group, a morpholin-4-yl group, a thiomorpholin-4-yl group or a piperazin-1-yl group optionally having one group selected from a following group $Z_p$).

The group $Z_p$ represents a $C_{1-6}$ alkyl group.

It is preferable that $X_p$ is a $C_{1-6}$ alkyl group, an ethyl group having one group selected from a following $A_p 2$ group, or a methyl group having one group selected from the $A_p 2$ group.

Herein, the $A_p 2$ group may be a group consisting of a 2-dimethylaminoethyl group, a 2-methoxyethyl group and a cyclopropylmethyl group.

More preferably, $X_p$ may be a cyclopropylmethyl group, a t-butyl group, a methyl group, a 2-dimethylaminoethyl group, or a 2-methoxyethyl group.

Then, a process for producing a boron compound which is capable of introducing an oxymethyl group into an aromatic ring will be described.

The boron compound can be produced by a coupling reaction between a compound such as a boronic acid derivative and a boronic acid ester as described below, and a compound having an oxymethyl group, which is usually known to a person skilled in the art.

A process for producing the compound (I) represented by the formula I and the compound (IV) represented by the formula IV will be explained. The compounds can be prepared, for example, by the following ⟨Producing Process A⟩ or ⟨Producing Process B⟩.

⟨Producing Process A⟩

The compound (I) represented by the formula I or the compound (IV) represented by the formula IV according to the present invention can be produced by the method described below, but the process for producing the present compound is not limited thereto.

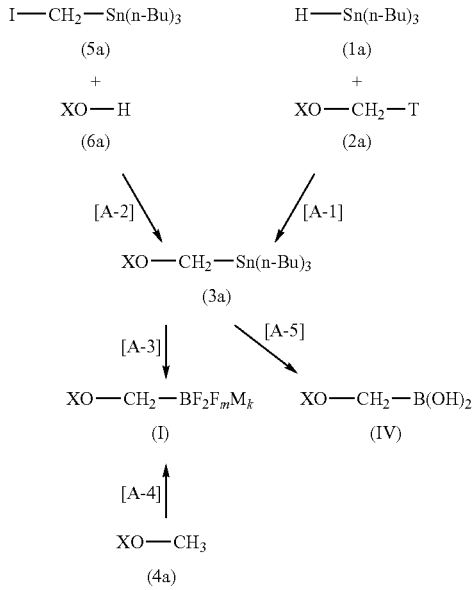

In the above-described formula, each definition of X, M, m and k is the same as defined above, respectively. T represents a leaving group such as a halogen atom, a methanesulfonyl group and the like.

[Step A-1]

The step A-1 is a step of reacting an anionized compound produced by a reaction of an organometallic reagent and a compound (1a) (CAS, No. 668-73-3), with a compound (2a) in a solvent, to produce a compound (3a).

The present step can be performed by a generally used method as described, for example, in fourth edition Experimental Chemical Course 25 (page 230 to page 233, Example 6. 84 etc.) or the like. Further, the present step can be more specifically performed by referring to reaction conditions, post-reaction procedures, purification methods and the like described in Example 2A-1 and the like described below.

The present reaction may be also performed under a stream or an atmosphere of an inert gas such as nitrogen, argon and the like.

As the compound (2a), known compounds, commercially available compounds, or compounds which can be easily produced from the commercially available compounds by a method which is usually performed by a person skilled in the art, can be used.

A solvent used in the present reaction is not particularly limited as far as it dissolves a starting material to some extent, and dose not inhibit the reaction. For example, ether solvents such as tetrahydrofuran, 1,2-dimethoxyethane, methyl-t-butyl ether, cyclopentyl methyl ether, diethyl ether, diisopropyl ether, dibutyl ether, dicyclopentyl ether and the like; aromatic hydrocarbon solvents such as benzene, toluene and the like; aliphatic hydrocarbon solvents such as heptane, hexane and the like; or a mixture thereof can be used. Suitable is tetrahydrofuran.

The organometallic reagent represents, for example, n-butyllithium, lithium diisopropylamide (LDA), lithium hexamethyldisilazide or the like, suitably lithium diisopropylamide (LDA). Lithium diisopropylamide (LDA) can be prepared from diisopropylamine and n-butyllithium.

A reaction time is usually different depending on a starting material, a solvent, other reagents used in a reaction, and a reaction temperature, and is appropriately selected. Suitably, after an anionized compound and a compound (2a) are mixed, the mixture is stirred at the following reaction temperature for 1 to 5 hours, more suitably for about 3 hours.

[Reaction Temperature in Anionizing Reaction]

A reaction temperature is usually different, depending on a starting material, a solvent and other reagents used in the reaction, and is appropriately selected. A temperature at addition of reagents may be −60° C. or lower (external temperature), more suitably −75° C. to −70° C. (internal temperature in reaction vessel).

A temperature after addition of reagents may be −10° C. to 10° C. (external temperature), more suitably about 5° C. (internal temperature in reaction vessel).

[Reaction Temperature in Reaction Between Anionized Compound and Compound (2a)]

A reaction temperature is usually different, depending on a starting material, a solvent and other reagents used in the reaction, and is appropriately selected. A temperature at addition of reagents may be −60° C. or lower (external temperature), more suitably −75° C. to −70° C. (internal temperature in reaction vessel).

A temperature after addition of reagents may be −10° C. to room temperature (external temperature), more suitably about room temperature (external temperature).

The compound (2a) can be used at a 0.8 to 1.2-fold mole amount, suitably a 1-fold mole amount relative to the compound (1a).

The organometallic reagent can be used at a 0.8 to 1.2-fold mole amount, suitably a 1-fold mole amount relative to the compound (1a).

[Step A-2]

The step A-2 is a step of reacting an anionized compound produced by a reaction of a base and a compound (6a), with a compound (5a) in a solvent, to produce a compound (3a).

The present step can be performed by a generally used method, such as the method described in WO 02/08226 (page 97, Example 48). In addition, the present step can be more specifically performed by referring to reaction conditions, post-reaction procedures, purification methods and the like described in Example 5A-3 described below.

The present reaction can be also performed under a stream or an atmosphere of an inert gas such as nitrogen, argon, and the like.

As the compound (6a), known compounds, commercially available compounds, or compounds which can be easily produced from the commercially available compounds by a method which is usually performed by a person skilled in the art, can be used.

As the compound (5a), the compound of Example 5A-2 described below, compounds which can be produced by the method described in Synthetic Communications, Vol. 24, No. 8, PP. 1117-1120, or the like can be used.

A solvent used in the present reaction is not particularly limited as far as it dissolves a starting material to some extent, and does not inhibit a reaction. For example, ether solvents such as tetrahydrofuran, 1,2-dimethoxyethane, methyl-t-butyl ether, cyclopentyl methyl ether, diethyl ether, diisopropyl ether, dibutyl ether, dicyclopentyl ether and the like; aromatic hydrocarbon solvents such as benzene, toluene and the like; amide solvents such as N,N-dimethylformamide, N-methylpyrrolidinone and the like; dimethyl sulfoxide; or a mixture thereof can be used. Suitable is tetrahydrofuran or N,N-dimethylformamide.

The base represents, for example, sodium hydride, potassium hydride or the like, suitably sodium hydride.

A reaction time is usually different depending on a starting material, a solvent, other reagents used in the reaction, and a reaction temperature, and is appropriately selected. Suitably, the compound (6a) and the base are mixed, and stirred at the following temperature for 30 to 60 minutes, and the compound (5a) is added to the mixture, followed by stirring at the following temperature for 1 to 12 hours.

[Reaction Temperature in an Ionization Reaction]

A reaction temperature is usually different, depending on a starting material, a solvent and other reagents used in the reaction, and is appropriately selected. A temperature at addition of reagents may be 5° C. or lower (external temperature), more suitably 0° C. to 5° C. (external temperature).

A temperature after addition of reagents may be 10° C. to room temperature (external temperature), more suitably room temperature (external temperature).

[Reaction Temperature in the Reaction Between an Ionized Compound and Compound (5a)]

A reaction temperature is usually different, depending on a staring material, a solvent and other reagents used in the reaction, and is appropriately selected. A temperature at addition of reagents may be 5° C. or lower (external temperature), more suitably 0° C. to 5° C. (external temperature).

A temperature after addition of reagents may be 10° C. to room temperature (external temperature), more suitably room temperature (external temperature).

The compound (5a) can be used at a 0.5 to 1.5-fold mole amount, suitably a 0.8 to 1.2-fold mole amount relative to the compound (6a).

The base can be used at a 0.5 to 1.5-fold mole amount, suitably a 0.8 to 1.2-fold mole amount relative to the compound (6a).

[Step A-3]

The step A-3 is a step of reacting an anionized compound produced by a reaction of an organometallic reagent and a compound (3a), with boronic acid ester (triisopropyl borate, trimethyl borate, 2-isopropoxy-4,4,5,5-tetramethyl-1,3,2-dioxaborane or the like), followed by reacting with a hydrogen fluoride salt (potassium hydrogen fluoride or sodium hydrogen fluoride) in a solvent, to produce a compound (I). The present step can be more specifically performed by referring to reaction conditions, post-reaction procedures, purification methods and the like described in Example 2A-2 or 8A-2 described below.

The present reaction can be also performed under a stream or an atmosphere of an inert gas such as nitrogen, argon and the like.

A solvent used in the present reaction is not particularly limited as far as it dissolves a staring material to some extent, and does not inhibit a reaction. For example, ether solvents such as tetrahydrofuran, 1,2-dimethoxyethane, methyl-t-butyl ether, cyclopentyl methyl ether, diethyl ether, diisopropyl ether, dibutyl ether, dicyclopentyl ether and the like; aromatic hydrocarbon solvents such as benzene, toluene and the like; aliphatic hydrocarbon solvents such as heptane, hexane and the like; or a mixture thereof can be used. Suitable is tetrahydrofuran.

The organometallic reagent represents, for example, n-butyllithium, sec-butyllithium, methyllithium or the like, suitably n-butyllithium.

The compound (I) can be obtained by the following two procedures, and the following (i) or (iii) procedure is preferable in order to suppress a side reaction (production of n-butyl trifluoroborate). In a case where a reaction (i) is difficult, e.g., in a case where an anion produced by reacting an organometallic reagent and a compound (3a) is unstable, the (iii) procedure is preferable. A temperature in the following (i), (ii) and (iii) indicates an internal temperature in a reaction mixture in any case.

(i) An organometallic reagent and a compound (3a) are stirred at −75 to −60° C. (suitably −75 to −70° C.) for 30 to 120 minutes (suitably 30 to 60 minutes) in a solvent. Then, to the mixture is added boronic acid ester at −75 to −70° C. and, thereafter, the mixture is stirred at 0° C. to room temperature (suitably 0 to 5° C.) for 10 to 120 minutes (suitably 20 to 80 minutes).

To the mixture is added a hydrogen fluoride salt at 0 to 5° C., thereafter, water is added at the same temperature, and a temperature of the reaction mixture is raised to room temperature, thereby, the compound (I) can be obtained.

(ii) An organometallic reagent and a compound (3a) are stirred at −75 to −60° C. (suitably −75 to −70° C.) for 30 to 120 minutes (suitably 30 to 60 minutes) in a solvent. Then, the mixture is added dropwise to a mixture of boronic acid ester and the solvent at −75 to −70° C. using a cannula and, thereafter, the mixture is stirred at 0° C. to room temperature (suitably 0 to 5° C.) for 10 to 120 minutes (suitably 20 to 80 minutes).

To the mixture is added a hydrogen fluoride salt at 0 to 5° C., thereafter, water is added at the same temperature, and a temperature of the reaction mixture is raised to room temperature, thereby, the compound (I) can be obtained.

(iii) To a mixture of boronic acid ester and a compound (3a) is added an organometallic reagent at −75 to −60° C. (suitably −75 to −70° C.) in a solvent, and the mixture is stirred at −75 to 5° C. (suitably 0 to 5° C.) for 10 to 120 minutes (suitably 20 to 60 minutes).

To the mixture is added a hydrogen fluoride salt at 0 to 5° C., thereafter, water is added at the same temperature, and a temperature of the reaction mixture is raised to room temperature, thereby, the compound (I) can be obtained.

The organometallic reagent can be used at a 0.8 to 1.2-fold mole amount, suitably a 1-fold mole amount relative to the compound to (3a).

The boronic acid ester can be used at a 1 to 2-fold mole amount, suitably a 1 to 1.2-fold mole amount relative to the compound (3a).

The hydrogen fluoride salt can be used at a 3 to 10-fold mole amount, suitably a 3 to 7-fold mole amount relative to the compound (3a).

[Step A-4]

The step A-4 is a step of reacting an anionized compound produced by a reaction of an organometallic reagent and a compound (4a), with boronic acid ester, followed by reacting with a hydrogen fluoride salt (potassium hydrogen fluoride or sodium hydrogen fluoride), to produce a compound (I).

In the present step, the reaction can be performed in a solvent, or using a large amount of the compound (4a) as a solvent. Alternatively, the present step can be performed in the presence of a base.

The present step can be performed by a generally used method described, for example, in fifth edition Experimental Chemical Course 18 (pages 20 to 23), Tetrahedron Letters, Vol. 24, No. 31, pp. 3165-3168, or the like. And, the present step can be more specifically performed by referring to reaction conditions, post-reaction procedures, purification methods and the like described in Example 1A described below.

The present reaction may be also performed under a stream or an atmosphere of an inert gas such as nitrogen, argon and the like.

As the compound (4a), known compounds, commercially available compounds, or compounds which can be easily produced from the commercially available compounds by a method which is usually performed by a person skilled in the art, can be used.

A solvent used in the present reaction is not particularly limited as far as it dissolves a starting material to some extent, and dose not inhibit the reaction. For example, aliphatic hydrocarbon solvents such as heptane, hexane and the like can be used. Suitably, a large amount of the compound (4a) may be used as a solvent.

The organometallic reagent represents t-butyllithium, sec-butyllithium or the like, suitably sec-butyllithium.

The base represents potassium t-butoxide, potassium sec-butoxide, potassium methoxide or the like, suitably potassium t-butoxide.

The following temperature indicates an internal temperature in a reaction mixture unless otherwise indicated.

To a mixture of a compound (4a) and a solvent is added an organometallic reagent at −75 to −60° C. (suitably-75 to −70° C.), and the mixture is stirred at −20 to 0° C. (suitably −10 to −5° C.) for 5 to 30 minutes (suitably 5 to 10 minutes). Then, to the mixture is added boronic acid ester at −75 to −70° C. and, thereafter, the mixture is stirred at 10° C. to room temperature (suitably room temperature) for 10 to 60 minutes (suitably 10 to 30 minutes).

To the mixture is added a hydrogen fluoride salt at 0 to 5° C. (external temperature), thereafter, water is added at the same temperature, and a temperature of the reaction mixture is raised to room temperature, thereby, the compound (I) can be obtained.

The base can be used suitably at a 0.6 to 1-fold mole amount relative to the organometallic reagent.

The boronic acid ester can be used at a 1 to 2-fold mole amount, suitably a 1 to 1.8-fold mole amount relative to the organometallic reagent.

Then, an example of using the compound (I) will be explained. By using the compound (I), compounds having various aromatic ring substrates can be produced.

⟨Producing Process B⟩

The compound (I) according to the present invention can be used as a reaction reagent under reaction conditions described below. However, use of the present compound as a reaction reagent is not limited to the reaction.

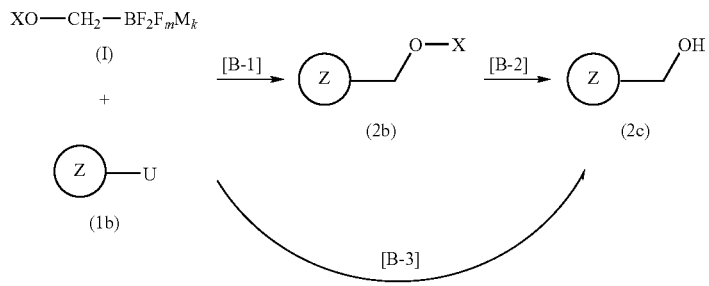

The hydrogen fluoride salt can be used at a 3 to 10-fold mole amount, suitably a 3 to 7-fold mole amount relative to the boronic acid ester.

[Step A-5]

The step A-5 is a step of reacting an anionized compound produced by a reaction of an organometallic reagent and a compound (3a), with boronic acid ester (triisopropyl borate, trimethyl borate, 2-isopropoxy-4,4,5,5-tetramethyl-1,3,2-dioxaborane or the like), followed by treating the resultant with a base in a solvent, to produce a compound (IV) which is a boric acid derivative according to the present invention. The present step can be more specifically performed by referring to reaction conditions, post-reaction procedures, purification methods and the like described in Example 16A-2 described below.

The present reaction can be also performed under a stream or an atmosphere of an inert gas such as nitrogen, argon and the like.

A solvent used in the present reaction is not particularly limited as far as it dissolves a staring material to some extent, and does not inhibit a reaction. For example, ether solvents such as tetrahydrofuran, 1,2-dimethoxyethane, methyl-t-butyl ether, cyclopentyl methyl ether, diethyl ether, diisopropyl ether, dibutyl ether, dicyclopentyl ether and the like; aromatic hydrocarbon solvents such as benzene, toluene and the like; aliphatic hydrocarbon solvents such as heptane, hexane and the like; or a mixture thereof can be used. Suitable is tetrahydrofuran.

The organometallic reagent represents, for example, n-butyllithium, methyllithium or the like, suitably n-butyllithium.

The base represents, for example, potassium hydroxide, sodium hydroxide or the like, suitably sodium hydroxide.

In a solvent, an organometallic reagent and a compound (3a) are stirred at −75 to −60° C. (suitably −75 to −70° C.) for 30 to 120 minutes (suitably 30 to 60 minutes). Then, to the mixture is added boronic acid ester at −75 to −70° C. and, thereafter, the mixture is stirred at 0° C. to room temperature (suitably 0 to 5° C.) for 10 to 120 minutes (suitably 20 to 80 minutes).

To the mixture is added a base at 10 to 40° C. (suitably room temperature), thereby, the compound (IV) can be obtained.

In the formula, each definition of X, M, m and k is the same as defined above.

Each Z represents an aromatic hydrocarbon ring (benzene, naphthalene or the like) or an aromatic heterocycle (pyridine, quinoline or the like), optionally having 1 to 4 groups selected from substituent group consisting of an alkoxy group, an alkyl group and a nitro group. U means a leaving group such as a halogen atom, a trifluoromethanesulfonyloxy group and the like.

[Step B-1]

The step B-1 is a step of reacting a compound (1b) and a compound (I) in a solvent, to produce a compound (2b).

In the present step, the reaction can be performed in the presence of a base, a palladium compound and a phosphine compound.

The present step can be performed by referring to reaction conditions, post-reaction procedures, and purification methods described in Examples B-1 to B-11 and B-13 described below.

The present reaction can be also performed under a stream or an atmosphere of an inert gas such as nitrogen, argon and the like.

As the compound (1b), known compounds, commercially available compounds, or compounds which can be easily produced from the commercially available compounds by a method which is usually performed by a person skilled in the art, can be used.

A solvent used in present reaction is not particularly limited as far as it dissolves a starting material to some extent, and does not inhibit a reaction. For example, ether solvents such as tetrahydrofuran, 1,2-dimethoxyethane, methyl-t-butyl ether, cyclopentyl methyl ether, diethyl ether, diisopropyl ether, dibutyl ether, dicyclopentyl ether and the like; aromatic hydrocarbon solvents such as benzene, toluene and the like; aliphatic hydrocarbon solvents such as heptane, hexane and the like; amide solvents such as N,N-dimethylformamide, N-methylpyrrolidinone and the like; dimethyl sulfoxide; or a mixture thereof can be used. Suitable is 1,4-dioxane or toluene.

The base represents, for example, potassium phosphate tribasic, cesium carbonate, cesium fluoride or the like, suitably cesium carbonate or potassium phosphate tribasic.

The palladium compound represents, for example, palladium (II) acetate, tris(dibenzylideneacetone)dipalladium (0), palladium carbon, bis(triphenylphosphine)palladium (II) chloride, bis(tri-t-butylphosphine)palladium (0), tetrakis (triphenylphosphine)palladium (0), 1,1'-bis(diphenylphosphinoferrocene)dichloropalladium (II) or the like, suitably palladium (II) acetate.

The phosphine compound represents, for example, triphenylphosphine, tri-o-tolylphosphine, tri-t-butylphosphine, tricyclohexylphosphine, diphenylphosphinoferrocene, 2-dicyclohexylphosphino-2',6'-dimethoxybiphenyl, 2-dicyclohexylphosphino-2',4',6'-triisopropylbiphenyl, 2-di-t-butylphosphino-2',4',6'-trisiopropylbiphenyl, 2-di-t-butylphosphinobiphenyl, 2-dicyclohexylphosphinobiphenyl, 2-dicyclohexylphosphino-2'-(N,N-dimethylamino)biphenyl, 2-di-t-butylphosphino-2'-(N,N-dimethylamino)biphenyl, 2,2'-bis(diphenylphosphino)-1,1'-binaphthyl, 1,2-bis(diphenylphosphino)ethane, 1,3-bis(diphenylphosphino)propane, 1,4-bis(diphenylphosphino)butane or the like, suitably diphenylphosphinoferrocene, triphenylphosphine, tri-o-tolylphosphine, 2,2'-bis(diphenylphosphino)-1,1'-binaphthyl, 1,4-bis (diphenylphosphino)butane, or 2-dicyclohexylphosphino-2', 6'-dimethoxybiphenyl.

A reaction time is usually different depending on a starting material, a solvent, and other reagents used in the reaction, and is appropriately selected. Suitably, after addition of reagents, the mixture is stirred at the following reaction temperature for suitably 1 to 72 hours, more suitably 4 to 12 hours.

A reaction temperature is usually different depending on a starting material, a solvent, and other reagents in the reaction, and is appropriately selected. The reaction temperature may be suitably 60° C. to 130° C. (external temperature), more suitably 95° C. to 105° C. (external temperature).

The compound (I) can be used at a 1 to 3-fold mole amount, suitably a 1 to 2-fold mole amount relative to the compound (1b).

The base can be used at a 1 to 4-fold mole amount, suitably a 2 to 3-fold mole amount relative to the compound (I).

The palladium compound can be used at a 0.001 to 0.5-fold mole amount, suitably a 0.05 to 0.2-fold mole amount relative to the compound (1b).

The phosphine compound can be used at a 0.001 to 3-fold mole amount, suitably a 0.05 to 1-fold mole amount relative to the compound (1b).

[Step B-2]

The step B-2 is a step of hydrolyzing a compound (2b) in the presents of an acid or a base, in a case where X of the compound (2b) is $R^5C(=O)$ ($R^5$ represents a hydrogen atom, a $C_{1-6}$ alkyl group or a $C_{3-8}$ cycloalkyl group), to obtain a compound (2c).

The present step can be performed under a hydrolysis condition which is usually known to a person skilled in the art.

[Step B-3]

The step B-3 is a step of obtaining a compound (2c) from a compound (2a) in a case where X of the compound (2a) is $R^5C(=O)$ ($R^5$ represents a hydrogen atom, a $C_{1-6}$ alkyl group or a $C_{3-8}$ cycloalkyl group).

The present step can be performed under the same condition as that of the step B-1. The present step can be more specifically performed by referring to reaction conditions, post-reaction procedures, purification methods and the like described in Example B-12 or B-14 described below.

⟨Producing Process C⟩

The compound (I) represented by the formula I according to the present invention can be also produced by the method described below.

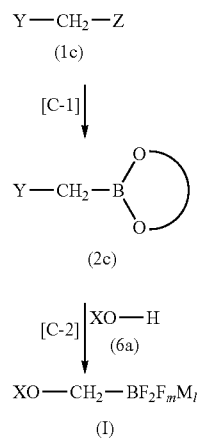

In the formula, X, M, m and k are as defined above, respectably. Y and Z each independently mean a halogen atom.

A group which is a part of the formula (2c) and is represented by the following formula X means cyclic boronic acid ester groups listed in the following formulae X-1 to X-6.

[Step C-1]

The step C-1 is a step of reacting an anionized compound produced by a reaction of an organometallic reagent and a compound (1c), with boronic acid ester, followed by adding an acid to neutralize the reaction mixture, and finally reacting with a diol such as pinacol and the like, to produce a compound (2c). The present step can be more specifically performed by referring to reaction conditions, post-reaction procedures, purification methods and the like described in Example C1 or C2 described below.

In the present reaction, an organometallic reagent is added to a mixture of the compound (1c) and boronic acid ester, and a reaction with boronic acid ester can be also performed at the same time with production of an anion of the compound (1c).

The present reaction can be also performed under a stream or an atmosphere of an inert gas such as nitrogen, argon and the like.

As the compound (1c), for example, chloroiodomethane, dibromomethane, bromoiodomethane or the like can be used. Suitable is chloroiodomethane, or dibromomethane.

A solvent used in the present invention is not particularly limited as far as it dissolves a starting material to some extent, and does not inhibit a reaction. For example, ether solvents such as tetrahydrofuran, 1,2-dimethoxyethane, methyl-t-butyl ether, cyclopentyl methyl ether, diethyl ether, diisopropyl ether, dibutyl ether, dicyclopentyl ether and the like; aromatic hydrocarbon solvents such as benzene, toluene and the like; aliphatic hydrocarbon solvents such as heptane, hexane and the like; or a mixture thereof can be used. Suitable is tetrahydrofuran.

The boronic acid ester represents, for example, trimethyl borate, triisopropyl borate or the like, suitably triisopropyl borate.

The organometallic reagent represents, for example, n-butyllithium, s-butyllithium or the like, suitably n-butyllithium.

The acid represents, for example, methanesulfonic acid, p-toluenesulfonic acid, hydrochloric acid-ethyl acetate solution, hydrochloric acid-methanol solution or the like, suitably methanesulfonic acid, or hydrochloric acid-ethyl acetate solution.

A reaction time is usually different depending on a starting material, a solvent, other reagents used in the reaction, and a reaction temperature, and is appropriately selected.

Suitably, a mixture of an anionized compound prepared from a compound (1c) and an organometallic reagent at −78° C. (external temperature), with boronic acid ester is stirred at the following reaction temperature for 1 to 3 hours. After neutralization of the mixture at the following temperature, subsequently a diol is added, and the mixture is stirred at the following temperature for 10 to 60 minutes.

[Reaction Temperature in the Reaction of Anionized Compound and Boronic Acid Ester]

A reaction temperature is usually different depending on a starting material, a solvent and other reagents used in the reaction, and is appropriately selected. A mixture of an anionized compound and boronic acid ester is stirred at 0° C. to room temperature (external temperature), more suitably at room temperature (external temperature).

[Reaction Temperature in the Neutralization Reaction and the Reaction with Diol]

A reaction temperature is usually different depending on a starting material, a solvent, and other reagents used in the reaction, and is appropriately selected. A temperature at a neutralization reaction and addition of a diol may be −20° C. to room temperature (external temperature), more suitably at 0° C. (external temperature).

A temperature after addition of a diol may be 0° C. to room temperature (external temperature), more suitably at room temperature (external temperature).

The boronic acid ester can be used at a 0.8 to 1.2-fold mole amount, suitably a 0.9 to 1-fold mole amount relative to the compound (1c).

The organometallic reagent can be used at a 0.8 to 1.2-fold mole amount, suitably a 0.8 to 1-fold mole amount relative to the compound (1c).

[Step C-2]

The step C-2 is a step of reacting an anionized compound produced by a reaction of a base and a compound (6a), with a compound (2c), followed by reacting with a hydrogen fluoride salt (potassium hydrogen fluoride, sodium hydrogen fluoride or the like), to produce a compound (I). The present step can be more specifically performed by referring to reaction conditions, post-reaction procedures, purification methods and the like described in Examples C3 to C15 described below.

The present step can be performed in the presence of an iodine compound such as potassium iodide, tetrabutylammonium iodide and the like.

The present reaction may be also performed under a stream or an atmosphere of an inert gas such as nitrogen, argon and the like.

As the compound (6a), known compounds, commercially available compounds, or compounds which can be easily produced from the commercially available compounds by a method which is usually performed by a person skilled in the art, can be used.

A solvent used in the present reaction is not particularly limited as far as it dissolves a starting material to some extent, and dose not inhibit the reaction. For example, ether solvents such as tetrahydrofuran, 1,2-dimethoxyethane, methyl-t-butyl ether, cyclopentyl methyl ether, diethyl ether, diisopropyl ether, dibutyl ether, dicyclopentyl ether and the like; aromatic hydrocarbon solvents such as benzene, toluene and the like; amide solvents such as N,N-dimethylformamide, N-methylpyrrolidinone and the like; dimethyl sulfoxide; or a mixture solvent thereof can be used. Suitable is tetrahydrofuran or N,N-dimethylformamide.

The base represents, for example, sodium hydride, potassium bis(trimethylsilyl)amide, potassium hydride or the like, suitably sodium hydride and potassium bis(trimethylsilyl) amide. In a case where X is $R^5C(=O)$ (the definition of $R^5$ is as defined above), as the base, potassium hydroxide, cesium carbonate, lithium hydroxide, sodium hydroxide or the like can be also used. Suitably is sodium hydroxide or potassium hydroxide.

A reaction time is usually different depending on a starting material, a solvent, other reagents used in the reaction, and a reaction temperature, and is appropriately selected. Suitably, after a reaction of anionizing a compound (6a), the mixture is stirred at the following temperature for 30 to 60 minutes, a compound (2c) is added to the mixture, and the mixture is stirred at the following temperature for 1 to 12 hours.

[Reaction Temperature in the Anionizing Reaction]

A reaction temperature is usually different depending on a starting material, a solvent, and other reagents used in the reaction, and is appropriately selected. A temperature at addition of the base may be 0° C. to room temperature (external temperature), more suitably 0° C. (external temperature).

A temperature after addition of the base is 0° C. to 70° C. (external temperature), more suitably room temperature to 50° C. (external temperature).

[Reaction Temperature in the Reaction Between Anionized Compound and Compound (2c)]

A reaction temperature is usually different depending on a starting material, a solvent, and other reagents used in the reaction, and is appropriately selected. A temperature at addition of the compound (2c) may be 0° C. to room temperature (external temperature), more suitably 0° C. (external temperature).

A temperature after addition of the compound (2c) may be room temperature to 100° C. (external temperature), more suitably room temperature to 70° C. (external temperature).

[Reaction temperature in the reaction of adding hydrogen fluoride Salt]

A reaction temperature is usually different depending on a starting material, a solvent, and other reagents used in the reaction, and is appropriately selected. A temperature at addition of reagents may be 0° C. to room temperature (external temperature), more suitably 0° C. (external temperature).

A temperature after addition of the reagent may be 0° C. to room temperature (external temperature), more suitably room temperature (external temperature)

The compound (6a) can be used at a 1 to 10-fold mole amount, suitably a 1 to 1.8-fold mole amount relative to the compound (2c).

The base can be used at a 1 to 2-fold mole amount, suitably a 1 to 1.8-fold mole amount relative to the compound (2c).

The hydrogen fluoride salt can be used at a 2 to 8-fold mole amount, suitably a 2 to 6-fold mole amount relative to the compound (2c).

When the hydrogen fluoride salt is added at a 1 to 2-fold mole amount relative to the compound (2c), a compound in which m is 0 in the general formula (I) (X can form a ring structure together with boron), a compound represented by the general formula (II) or (III) can be obtained.

In a case where M in the compound (I) is an alkali metal, the reaction with tetraalkylammonium hydroxide, tetraalkylphosphonium hydroxide or the like may result in the compound (I) in which M represents $N(R^1)(R^2)(R^3)(R^4)$ or $P(R^1)(R^2)(R^3)(R^4)$ ($R^1$, $R^2$, $R^3$ and $R^4$ each independently represents a $C_{1-6}$ alkyl group or a $C_{7-15}$ aralkyl group). The present step can be performed by referring to Tetrahedron Letters, Vol. 42, pp. 9099-9103 and, more specifically, can be performed by referring to reaction conditions, post-reaction procedures, purification methods and the like described in Example 12A described below. The tetraalkylammonium hydroxide is, for example, tetrabutylammonium hydroxide. The tetraalkylphosphonium hydroxide is, for example, tetrabutylphosphonium hydroxide.

As a solvent used in the present reaction, a mixture solvent of dichloromethane or chloroform and water can be used.

A reaction time may be 1 minute to 30 minutes at room temperature (external temperature), suitably 1 to 5 minutes.

A reaction temperature may be 10 to 50° C., suitably around room temperature (external temperature).

Alternatively, in the present step, by treatment with a base as in the step A-5 without adding a hydrogen fluoride salt, the compound represented by the formula (IV) can be obtained.

After completion of the reaction of the above each method, and each step, an objective compound of each step can be collected from a reaction mixture according to a conventional method.

For example, when a whole reaction mixture is liquid, a reaction mixture is optionally returned to room temperature, or an acid, an alkali, an oxidizing agent or a reducing agent is appropriately added to neutralize under cooling (ice cooling to −78° C.), an organic solvent such as water and ethyl acetate which is not miscible, and does not react with an objective compound is added and a layer containing the objective compound is separated. Then, a solvent which is not miscible with the resulting layer, and does not react with the objective compound is added, a layer containing the objective compound is washed, and the layer is separated. In addition, when the layer is an organic layer, the layer is dried using a drying agent such as anhydrous magnesium sulfate or anhydrous sodium sulfate, and the solvent is distilled off to collect the objective compound. On the other hand, when the layer is an aqueous layer, the layer is electrically desalted, and lyophilized, thereby, the objective compound can be collected.

In addition, when a whole reaction mixture is liquid, and if possible, an objective compound can be collected only by distilling off substances other than the objective compound (e.g. solvent, reagent or the like) under a normal pressure or reduced pressure.

In addition, when a whole reaction mixture is liquid, and if possible, a reaction mixture can be purified by using various chromatographies (thin layer chromatography, column chromatography or the like) to collect the objective compound.

Further, when only an objective compound is precipitated as a solid, or when the whole reaction mixture is liquid, and only an objective compound is precipitated as a solid during a process of collection, first, an objective compound is filtered by a filtration method, a filtered objective compound is washed with an organic solvent or an inorganic solvent such as water, and is dried. In addition, by treating a mother liquor as in the case where the whole reaction mixture is liquid, an objective compound can be further collected.

In addition, further, when only a reagent or a catalyst is present as a solid, or when the whole reaction mixture is liquid, and only a reagent or a catalyst is newly precipitated as a solid during a process of collection, and an objective compound is dissolved in a solution, first, the reagent or the catalyst is filtered off by a filtration method. The reagent or catalyst which has been filtered off is washed with a suitable organic or inorganic solvent, the resulting washing solution is combined with another liquor, and the resulting mixed solution is treated as in a case where the whole reaction mixture is liquid, thereby, an objective compound can be collected.

In particular, when substances other than an objective compound contained in the reaction mixture do not inhibit a reaction of a next step, the reaction mixture as it is may be used in the next step without particularly isolating the objective compound.

In order to improve a purity of the objective compound collected by the Producing Process A or C, a recrystallization method, various chromatography methods, or a distillation method can be appropriately performed. When the collected objective compound is a solid, usually, a purity of the objective compound can be improved by a recrystallization method. In the recrystallization method, a single solvent or a mixture of plural solvents which do not react with the objective compound can be used. Specifically, first, the objective compound is dissolved in a single or plural solvents which do not react with an objective compound at room temperature or under heating. By cooling the resulting mixed solution with ice-water or the like, or allowing to stand it at room temperature, the objective compound can be precipitated from the mixed solution.

When the collected objective compound is liquid, a purity of the objective compound can be improved by various chro matography methods. Generally, weakly acidic silica gels such as silica gel 60 (70 to 230 mesh or 340 to 400 mesh) manufactured by Merck & Co., Inc. and silica gel 60 (0.040 to 0.050 mm) manufactured by Kanto Chemical Co., Inc. can be used. When the objective compound is acidic and unstable, neutral silica gel 60N (0.10 to 0.21 mm) manufactured by Kanto Chemical Co., Inc. may be used. When the objective compound has basicity, propylamine-coated silica gel (NH-silica gel column chromatography) (200 to 350 mesh) manufactured by Fuji Silysia Chemical Ltd. may be used. In addition, when the objective compound has a structure of a zwitterion, or when elution with a highly polar solvent such as methanol and the like is necessary, NAM-200H or NAM-300H manufactured by NAM Laboratory may be used. Using these silica gels, the objective compound is dissolved with single or plural solvents which do not react with the objective compound, and the solvent is distilled off, thereby, the objective compound with an improved purity can be obtained.

When the collected objective compound is liquid, a purity of the objective compound may be also improved by a distillation method. In the distillation method, the objective compound can be distilled by subjecting the objective compound to reduced pressure at room temperature or under heating.

The foregoing are representative embodiments of a process for producing the compound (I) according to the present invention. Raw material compound/various reagents in the production of the present compound may form a salt or a hydrate or a solvate, and all of them are different depending on a starting raw material, a solvent used and the like, and are not particularly limited as far as they do not inhibit a reaction. It goes without saying that a solvent used is different depending on a starting raw material, a reagent and the like, and is not particularly limited as far as it does not inhibit a reaction and dissolves a starting substance to some extent. When the compound (I) according to the present invention is obtained as a free compound, it can be converted into the state of a salt which may be formed by the compound (I), or a solvate thereof, according to a conventional method.

When the compound (I) according to the present invention is obtained as a solvate of the compound (I), a free compound of the above compound (I) can be converted.

Various isomers (e.g. geometric isomer, optical isomer, rotation isomer, stereoisomer, tautomer or the like) obtained regarding the compound (I) according to the present invention can be purified and isolated using the normal separation method, for example, recrystallization, a diastereomer salt method, an enzyme resolution method, various chromatographies (e.g. thin layer chromatography, column chromatography, gas chromatography or the like).

EXAMPLES

The present invention will be illustrated by way of following Examples, but the present invention is not limited thereto.

In the following Examples, "A" indicates an example of the present invention which is produced by the above-described Producing Process A. Further, "B" indicates an example of using the present compound in accordance with the above-described Producing Process B. More, "C" indicates an example of the compound of the present invention which is produced by the above-described Producing Process C.

Example 1A

Synthesis of potassium t-butoxymethyl trifluoroborate

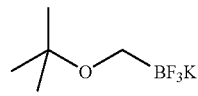

To a mixture of t-butyl methyl ether (30 ml) and potassium t-butoxide (330 mg, 3.0 mmol) was added dropwise sec-butyllithium (5.0 ml, 4.9 mmol) at −78° C. (external temperature). The mixture was raised to an internal temperature of −10° C., stirred for 5 minutes, and cooled again to −78° C. (external temperature). Thereafter, to the mixture was added dropwise triisopropyl borate (2.0 ml, 8.5 mmol) at −78° C. (external temperature), and the reaction mixture was stirred at room temperature for 30 minutes. To the reaction mixture were added tetrahydrofuran (60 ml) and potassium hydrogen fluoride (2.7 g, 34 mmol) at 0° C. (external temperature). Then, water (30 ml) was added dropwise over 15 minutes. The reaction mixture was raised to room temperature, and the solvent was distilled off under reduced pressure. The resulting residue was washed with diethyl ether (100 ml). To the solid was added acetone (200 ml), followed by filtration. After the solvent was distilled off from the filtrate under reduced pressure, recrystallization with acetonitrile afforded the title compound (150 mg, 0.77 mmol, 15%).

$^1$H-NMR Spectrum (DMSO-$d_6$) δ (ppm): 1.15 (9H, s), 2.30 (2H, q, J=5.5 Hz).

Example 2A

Synthesis of potassium methoxymethyl trifluoroborate

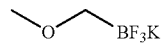

(2A-1) Tributyl-methoxymethyl-tin

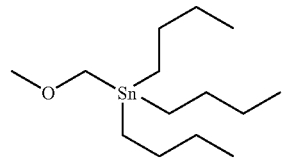

To a mixture of diisopropylamine (9.4 ml, 67 mmol) and tetrahydrofuran (150 ml) was added dropwise n-butyllithium (2.4M n-hexane solution, 25 ml, 61 mmol) at −78° C. (external temperature) Then, the reaction mixture was stirred for 30 minutes. To the mixture was added dropwise tributyltin hydride (16 ml, 61 mmol) at −78° C. (external temperature). Then, the reaction mixture was stirred at 0° C. (external temperature) for 30 minutes. After the reaction mixture was cooled at −78° C. (external temperature), chloromethyl methyl ether (4.6 ml, 61 mmol) was added dropwise to the reaction mixture. After the mixture was stirred at room temperature (external temperature) for 1 hour, water and diethyl ether were added to the reaction mixture, and the organic layer was separated. The organic layer was washed with an aqueous saturated sodium chloride solution, and the solvent was distilled off under reduced pressure. The residue was purified by neutral silica gel column chromatography (heptane:ethyl acetate=30:1) to obtain the title compound (18 g, 0.52 mmol, 86%).

$^1$H-NMR Spectrum (CDCl$_3$) δ (ppm): 0.88-0.93 (15H, m), 1.26-1.35 (6H, m), 1.47-1.55 (6H, m), 3.30 (3H, s), 3.71 (2H, t, J=6.8 Hz).

(2A-2) Potassium methoxymethyl trifluoroborate

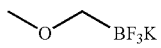

To a mixture of tributyl-methoxymethyl-tin (360 mg, 1.1 mmol) and tetrahydrofuran (3 ml) was added dropwise n-butyllithium (1.5M n-hexane solution, 0.77 ml, 1.2 mmol) at −78° C. (external temperature). The reaction mixture was stirred at the same temperature for 30 minutes. The mixture was added dropwise to a mixture of triisopropylborate (0.30 ml, 1.3 mmol) and tetrahydrofuran (5 ml) using a cannula at −78° C. (external temperature). The reaction mixture was stirred at room temperature for 20 minutes. To the mixture was added potassium hydrogen fluoride (0.51 g, 6.5 mmol) at 0° C. (external temperature) Then, water (60 ml) was added dropwise to the reaction mixture. The reaction mixture was raised to room temperature, and the solvent was distilled off under reduced pressure. The resulting residue was washed with diethyl ether. To the residue was added acetone, followed by filtration. After the solvent was distilled off from the filtrate under reduced pressure, the resulting residue was recrystallized using acetone to obtain the title compound (30 mg, 0.20 mmol, 18%).

$^1$H-NMR Spectrum (DMSO-d$_6$) δ (ppm): 2.39-2.43 (2H, m), 3.05 (3H, s).

Example 3A

Synthesis of potassium ethoxy methyl trifluoroborate

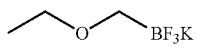

(3A-1) Tributyl-ethoxymethyl-tin

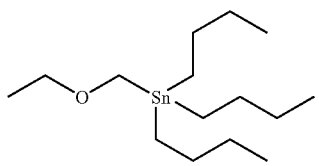

To a mixture of diisopropylamine (2.1 ml, 15 mmol) and tetrahydrofuran (30 ml) was added dropwise n-butyllithium (2.4M n-hexane solution, 5.0 ml, 12 mmol) at −78° C. (external temperature). Then, the reaction mixture was stirred for 30 minutes. To the mixture was added dropwise tributyltin hydride (3.3 ml, 12 mmol) at −78° C. (external temperature). Then, the reaction mixture was stirred at 0° C. (external temperature) for 40 minutes. The reaction mixture was cooled to −78° C. (external temperature), and ethoxymethyl chloride (1.1 ml, 12 mmol) was added dropwise to the reaction mixture. After the reaction mixture was raised to room temperature, to the reaction mixture were added diethyl ether and an aqueous ammonium chloride solution, and the organic layer was separated. The organic layer was washed with an aqueous saturated sodium chloride solution, and the solvent was distilled off under reduced pressure. The residue was purified by neutral silica gel column chromatography (heptane:diethyl ether=30:1) to obtain the title compound (2.8 g, 7.9 mmol, 66%).

$^1$H-NMR Spectrum (CDCl$_3$) δ (ppm): 0.87-0.92 (15H, m), 1.16 (3H, t, J=7.0 Hz), 1.26-1.35 (6H, m), 1.43-1.55 (6H, m), 3.36 (2H, q, J=7.0 Hz), 3.74 (2H, t, J=6.5 Hz).

(3A-2) Potassium ethoxymethyl trifluoroborate

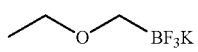

To a mixture of tributyl-ethoxymethyl-tin (1.0 g, 2.9 mmol) and tetrahydrofuran (10 ml) was added dropwise n-butyllithium (1.5M n-hexane solution, 2.0 ml, 3.2 mmol) at −78° C. (external temperature). Then, the reaction mixture was stirred at the same temperature for 30 minutes. The reaction mixture was added dropwise to a mixture of triisopropyl borate (0.73 ml, 3.2 mmol) and tetrahydrofuran (10 ml) by cannulation at −78° C. (external temperature). The reaction temperature was stirred at room temperature for 30 minutes. To the mixture was added potassium hydrogen fluoride (1.3 g, 17 mmol) at 0° C. (external temperature). Then, water (10 ml) was added dropwise to the reaction mixture. The reaction mixture was raised to room temperature, and the solvent was distilled off under reduced pressure. The resulting residue was washed with diethyl ether (50 ml). To this residue was added acetone (100 ml), followed by filtration. The solvent was distilled off from the filtrate under reduced pressure, and the residue was recrystallized using acetonitrile to obtain the title compound (150 mg, 0.90 mmol, 32%).

$^1$H-NMR Spectrum (DMSO-d$_6$) δ (ppm): 0.99 (3H, t, J=7.0 Hz), 2.42 (2H, q, J=5.6 Hz), 3.18 (2H, q, J=7.0 Hz).

Example 4A

Synthesis of potassium (2-methoxyethoxymethyl) trifluoroborate

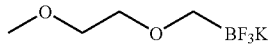

(4A-1) Tributyl-(2-methoxyethoxymethyl)-tin

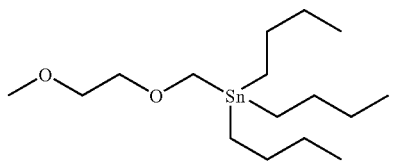

To a mixture of diisopropylamine (2.1 ml, 15 mmol) and tetrahydrofuran (30 ml) was added dropwise n-butyllithium (2.4M n-hexane solution, 5.0 ml, 12 mmol) at −78° C. (external temperature). Then, the reaction mixture was stirred for 30 minutes. To the mixture was added dropwise tributyltin hydride (3.3 ml, 12 mmol) at −78° C. (external temperature).

Then, the reaction mixture was stirred at 0° C. (external temperature) for 40 minutes. After the reaction mixture was cooled at −78° C. (external temperature), to the reaction mixture was added dropwise 2-methoxyethoxymethyl chloride (1.4 ml, 12 mmol). After a temperature was raised to room temperature, to the reaction mixture were added diethyl ether and an aqueous ammonium chloride solution, and the organic layer was separated. The organic layer was washed with an aqueous saturated sodium chloride solution, and the solvent was distilled off under reduced pressure. The residue was purified by neutral silica gel column chromatography (heptane:ethyl acetate=20:1) to obtain the title compound (2.6 g, 6.9 mmol, 57%).

$^{1}$H-NMR Spectrum (CDCl$_{3}$) δ (ppm): 0.82-0.99 (15H, m), 1.25-1.35 (6H, m), 1.43-1.57 (6H, m), 3.38 (3H, s), 3.46-3.49 (2H, m), 3.51-3.53 (2H, m), 3.79 (2H, t, J=6.4 Hz).

(4A-2) Potassium (2-methoxyethoxymethyl) trifluoroborate

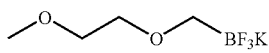

To a mixture of tributyl-(2-methoxyethoxymethyl)-tin (1.0 g, 2.6 mmol) and tetrahydrofuran (10 ml) was added n-butyllithium (1.5M n-hexane solution, 1.9 ml, 2.9 mmol) at −78° C. (external temperature). The reaction mixture was stirred at the same temperature for 45 minutes. To the reaction mixture was added dropwise a solution of triisopropyl borate (0.67 ml, 2.9 mmol) in tetrahydrofuran (10 ml) at −78° C. (external temperature). Then, the reaction mixture was stirred at room temperature for 15 minutes. To the mixture was added potassium hydrogen fluoride (1.2 g, 16 mmol) at 0° C. (external temperature). Then, water (10 ml) was added dropwise to the reaction mixture. After the reaction mixture was raised to room temperature, the solvent was distilled off under reduced pressure. The resulting residue was washed with diethyl ether. To this residue was added acetone, followed by filtration. The solvent was distilled off from the filtrate under reduced pressure to obtain the title compound (276 mg, 1.4 mmol, 53%).

$^{1}$H-NMR Spectrum (DMSO-d$_{6}$) δ (ppm): 3.37-3.27 (4H, m), 3.21 (3H, s), 2.50-2.44 (2H, m).

Example 5A

Synthesis of potassium cyclopropylmethoxymethyl trifluoroborate

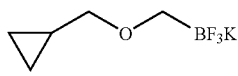

(5A-1) Tributylstannyl-methanol

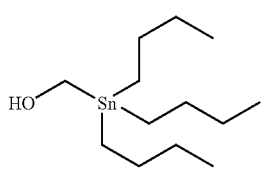

To a mixture of diisopropylamine (62 ml, 0.44 mol) and tetrahydrofuran (1000 ml) were added dropwise n-butyllithium (2.6M n-hexane solution, 100 ml, 0.26 mol) and n-butyllithium (1.6M n-hexane solution, 95 ml, 0.15 mol) at −78° C. (external temperature). Then, the reaction mixture was stirred for 30 minutes. To the mixture was added dropwise tributyltin hydride (100 ml, 0.37 mol) at −78° C. (external temperature). Then, the reaction mixture was stirred at 0° C. (external temperature) for 60 minutes. After the reaction mixture was cooled at −78° C. (external temperature) and paraformaldehyde (13 g, 0.15 mol) was added to the reaction mixture. The reaction mixture was gradually raised to room temperature, and then, the reaction mixture was stirred at room temperature overnight. To the reaction mixture were added water, an aqueous ammonium chloride solution and diethyl ether, and the organic layer was separated. The organic layer was sequentially washed with an aqueous saturated sodium bicarbonate solution and an aqueous saturated sodium chloride solution. The organic layer was separated, and the solvent was distilled off under reduced pressure. The residue was purified by neutral silica gel column chromatography (heptane:diethyl ether=4:1) to obtain the title compound (95 g, 0.30 mol, 80%).

$^{1}$H-NMR Spectrum (CDCl$_{3}$) δ (ppm): 0.88-0.94 (15H, m), 1.27-1.36 (6H, m), 1.49-1.55 (6H, m), 4.02 (2H, dd, J=1.8, 6.6 Hz).

(5A-2) Tributyl-iodomethyl-tin

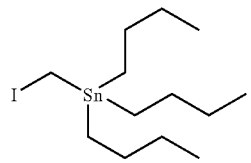

To a mixture of triphenylphosphine (70 g, 0.27 mol) and tetrahydrofuran (500 ml) was added dropwise a mixture of N-iodosuccinimide (60 g, 0.27 mmol) and tetrahydrofuran (500 ml) at 0° C. (external temperature). Then, the reaction mixture was stirred at 0° C. (external temperature) for 30 minutes. To the mixture was added dropwise tributylstannylmethanol (71 g, 0.22 mol) at 0° C. (external temperature). Then, the reaction mixture was stirred at 0° C. (external temperature) for 20 minutes. The reaction mixture was stirred at room temperature overnight. To the reaction mixture were added diethyl ether and water, and the organic layer was separated. The organic layer was sequentially washed with an aqueous saturated sodium thiosulfate solution and an aqueous saturated sodium chloride solution. The organic layer was separated, and the solvent was distilled off under reduced pressure. To the residue was added heptane (400 ml), followed by filtration. The solvent was distilled off under reduced pressure, and the residue was purified by silica gel column chromatography (heptane) to obtain the title compound (90 g, 0.21 mol, 94%).

$^{1}$H-NMR Spectrum (CDCl$_{3}$) δ (ppm): 0.91 (9H, t, J=7.2 Hz), 0.96-1.00 (6H, m), 1.28-1.37 (6H, m), 1.49-1.56 (6H, m), 1.94 (2H, t, J=8.9 Hz).

(5A-3) Tributyl-cyclopropylmethoxymethyl-tin

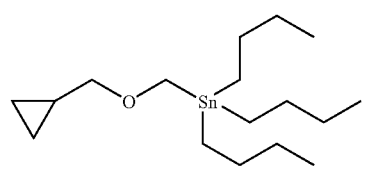

To a mixture of sodium hydride (66%, 250 mg, 7.0 mmol) and tetrahydrofuran (20 ml) were added cyclopropylmethanol (0.56 ml, 7.0 mmol) and N,N-dimethylformamide (20 ml) at 0° C. (external temperature). Then, the reaction mixture was stirred at room temperature for 40 minutes. To the reaction mixture was added dropwise tributyl-iodomethyl-tin (2.0 g, 4.6 mmol) at 0° C. (external temperature). Then, the reaction mixture was stirred at room temperature overnight. To the reaction mixture were added heptane and water, and the organic layer was separated.

The organic layer was washed with an aqueous saturated sodium chloride solution, and the solvent was distilled off under reduced pressure. The residue was purified by silica gel column chromatography (heptane:ethylacetate=20:1) to obtain the title compound (1.6 g, 4.3 mmol, 93%).

$^1$H-NMR Spectrum (CDCl$_3$) δ(ppm): 0.17-0.21 (2H, m), 0.47-0.51 (2H, m), 0.84-0.98 (15H, m), 1.02-1.05 (1H, m), 1.26-1.35 (6H, m), 1.47-1.53 (6H, m), 3.16 (2H, d, J=6.8 Hz), 3.77 (2H, t, J=6.2 Hz).

(5A-4) Potassium cyclopropylmethoxymethyl trifluoroborate

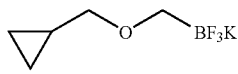

To a mixture of tributyl-cyclopropylmethoxymethyl-tin (1.45 g, 3.86 mmol) and tetrahydrofuran (28 ml) was added dropwise n-butyllithium (1.54M n-hexane solution, 2.51 ml, 3.87 mmol) at −78° C. (external temperature). Then, the reaction mixture was stirred at the same temperature for 30 minutes. To the mixture was added dropwise triisopropyl borate (980 μl, 4.25 mmol) at −78° C. (external temperature). Then, the reaction mixture was stirred at 0° C. (external temperature) for 20 minutes. To the mixture was added potassium hydrogen fluoride (1.81 g, 23.2 mmol) at 0° C. (external temperature), and then, water (10 ml) was added dropwise to the reaction mixture. The reaction mixture was raised to room temperature, and the solvent was distilled off under reduced pressure. The resulting residue was washed with diethyl ether (50 ml). To this residue was added acetone (70 ml), followed by filtration. The solvent was distilled off from the filtrate under reduced pressure to obtain the title compound (327 mg, 1.70 mmol, 44%) as a colorless solid.

$^1$H-NMR Spectrum (DMSO-d$_6$) δ (ppm): 0.02 (2H, dd, J=4.4 Hz, 9.2 Hz), 0.31-0.35 (2H, m), 0.80-0.85 (1H, m), 2.40 (2H, q, J=5.2 Hz), 2.95 (2H, d, J=6.8 Hz).

Example 6A

Synthesis of potassium {[2-(dimethylamino)ethoxy]methyl} trifluoroborate

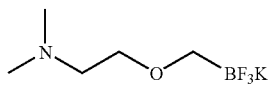

(6A-1) N,N-dimethyl-2-[(tri-n-butylstannyl)methoxy]ethanamine

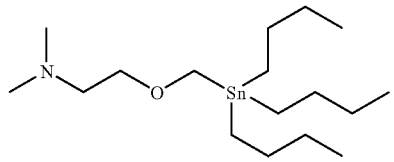

To a mixture of sodium hydride (60%, 278 mg, 7.0 mmol) and tetrahydrofuran (20 ml) was added 2-dimethylaminoethanol (0.70 ml, 7.0 mmol) at 0° C. (external temperature). Then, the reaction mixture was stirred at room temperature for 30 minutes. To the reaction mixture was added dropwise a mixture of tributyl-iodomethyl-tin (2.0 g, 4.6 mmol) and tetrahydrofuran (5 ml)-N,N-dimethylformamide (20 ml) at 0° C. (external temperature). Then, the reaction mixture was stirred at room temperature for 1 hour. The reaction mixture was poured into water, ethyl acetate was added, and the organic layer was separated. The organic layer was washed with water and an aqueous saturated sodium chloride solution, and dried over anhydrous magnesium sulfate. Then, the solvent was distilled off under reduced pressure. The residue was purified with silica gel column chromatography (heptane:ethyl acetate=19:1, NH silica gel) to obtain the title compound (1.7 g, 4.3 mmol, 93%).

$^1$H-NMR Spectrum (CDCl$_3$) δ (ppm): 0.81-0.98 (15H, m), 1.25-1.34 (6H, m), 1.40-1.60 (6H, m), 2.26 (6H, s), 2.47 (2H, t, J=6.0 Hz), 3.41 (2H, t, J=6.0 Hz), 3.75 (2H, t, J=6.4 Hz).

(6A-2) Potassium {[2-(dimethylamino)ethoxy]methyl} trifluoroborate

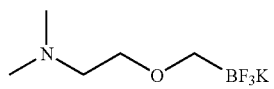

To a mixture of N,N-dimethyl-2-[(tri-n-butylstannyl) methoxy]ethanamine (1.7 g, 4.2 mmol) and tetrahydrofuran (36 ml) was added dropwise n-butyllithium (2.59M n-hexane solution, 1.8 ml, 4.7 mmol) at −78° C. (external temperature). Then, the reaction mixture was stirred at the same temperature for 30 minutes. The mixture was added dropwise to a mixture of triisopropyl borate (1.1 ml, 4.7 mmol) and tetrahydrofuran (10 ml) cooled at −78° C. (external temperature) via cannula over 20 minutes. Then, the reaction mixture was raised to room temperature, and stirred for 1 hour. To the mixture was added potassium hydrogen fluoride (2.0 g, 25 mmol) at 0° C. (external temperature), and then, water (10 ml) was added dropwise to the reaction mixture. After the mixture was stirred at 0° C. (external temperature) for 30 minutes, the reaction mixture was raised to room temperature, and the solvent was distilled off under reduced pressure. The resulting residue was washed with diethyl ether (100 ml). To this residue was added acetone (50 ml), followed by filtration. The solvent was distilled off from the filtrate under reduced pressure, and to the residue was added hexane, followed by crystallization and washing to obtain the title compound (285 mg, 1.2 mmol, 29%).

$^1$H-NMR Spectrum (DMSO-d$_6$) δ (ppm): 2.13 (6H, s), 2.33 (2H, t, J=6.0 Hz), 2.49-2.53 (2H, m), 3.27 (2H, t, J=6.0 Hz).

Example 7A

Synthesis of potassium cyclobutoxymethyl trifluoroborate

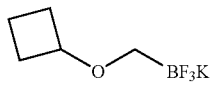

(7A-1) Tributyl-cyclobutoxymethyl-tin

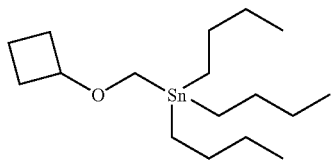

To a mixture of sodium hydride (66%, 250 mg, 7.0 mmol) and tetrahydrofuran (20 ml) were added cyclobutanol (0.55 ml, 7.0 mmol) and N,N-dimethylformamide (20 ml) at 0° C. (external temperature). Then, the reaction mixture was stirred at room temperature for 40 minutes. To the reaction mixture was added dropwise tributyl-iodomethyl-tin (2.0 g, 4.6 mmol) at 0° C. (external temperature). Then, the reaction mixture was stirred at room temperature overnight. To the reaction mixture were added heptane and water, and the organic layer was separated. The organic layer was washed with an aqueous saturated sodium chloride solution, and then, the solvent was distilled off under reduced pressure. The residue was purified by silica gel column chromatography (heptane:ethylacetate=20:1) to obtain the title compound (1.6 g, 4.3 mmol, 92%).

$^1$H-NMR Spectrum (CDCl$_3$) δ (ppm): 0.81-0.98 (15H, m), 1.26-1.35 (6H, m), 1.43-1.57 (7H, m), 1.65-1.70 (1H, m), 1.80-1.87 (2H, m), 2.14-2.21 (2H, m), 3.57 (2H, dd, J=7.3, 7.0 Hz), 3.68-3.76 (1H, m).

(7A-2) Potassium cyclobutoxymethyl trifluoroborate

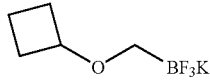

To a mixture of tributyl-cyclobutoxymethyl-tin (1.0 g, 2.7 mmol) and tetrahydrofuran (10 ml) was added dropwise n-butyllithium (1.5M n-hexane solution, 1.7 ml, 2.7 mmol) at −78° C. (external temperature). Then, the reaction mixture was stirred at the same temperature for 60 minutes. To the mixture was added dropwise a solution of triisopropyl borate (0.80 ml, 3.5 mmol) in tetrahydrofuran (10 ml) at −78° C. (external temperature). Then, the reaction mixture was stirred at room temperature for 5 minutes. To the reaction mixture was added potassium hydrogen fluoride (1.25 g, 16 mmol) at 0° C. (external temperature), and then, the reaction mixture was stirred at room temperature for 50 minutes. To the compound was added dropwise water (10 ml) at room temperature, and then, the reaction mixture was further stirred at the same temperature for 50 minutes. The solvent was distilled off from the reaction mixture under reduced pressure. The resulting residue was washed with diethyl ether. To this residue was added acetone, followed by filtration. The solvent was distilled off from the filtrate under reduced pressure to obtain the title compound (214 mg, 1.1 mmol, 42%).

$^1$H-NMR Spectrum (DMSO-d$_6$) δ (ppm): 3.60 (1H, quin, J=6.8 Hz), 2.31 (2H, q, J=5.6 Hz), 2.08-1.99 (2H, m), 1.73-1.61 (2H, m), 1.58-1.48 (1H, m), 1.42-1.30 (1H, m).

Example 8A

Synthesis of potassium 2-piperidin-1-yl ethoxymethyl trifluoroborate

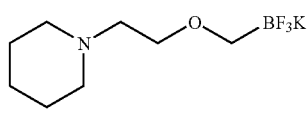

(8A-1) 1-(2-Tributylstannylmethoxyethyl)piperidine

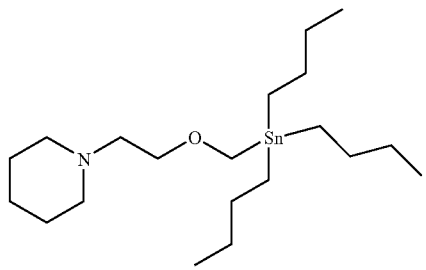

To a mixture of 1-piperidinemethanol (1.3 g, 10 mmol) and tetrahydrofuran (30 ml) was added sodium hydride (60%, 418 mg, 10 mmol) at 0° C. (external temperature), followed by stirring at room temperature for 30 minutes. Then, to the reaction mixture was added dropwise a mixture of tributyl-iodomethyl-tin (3.0 g, 7.0 mmol), tetrahydrofuran (5 ml), and N,N-dimethylformamide (30 ml) at 0° C. Then, the reaction mixture was stirred at room temperature for 1 hour. To the reaction mixture were added water and ethyl acetate, and the organic layer was separated. The organic layer was sequentially washed with water and an aqueous saturated sodium chloride solution, and dried over anhydrous magnesium sulfate. The solvent was distilled off under reduced pressure. The residue was purified by silica gel column chromatography (heptane:ethyl acetate=20:1, NH silica gel) to obtain the title compound (2.1 g, 4.9 mmol, 70%).

$^1$H-NMR Spectrum (CD$_3$OD) δ (ppm): 0.87-0.91 (15H, m), 1.25-1.34 (6H, m), 1.39-1.44 (2H, m), 1.46-1.52 (6H, m), 1.54-1.60 (4H, m), 2.42 (4H, brs), 2.52 (2H, t, J=6.0 Hz), 3.46 (2H, t, J=6.0 Hz), 3.73 (2H, s).

(8A-2) Potassium 2-piperidin-1-ylethoxymethyl trifluoroborate

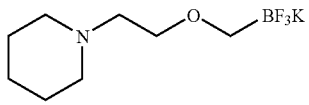

To a mixture of 1-(2-tributylstannylmethoxyethyl)piperidine (2.1 g, 4.9 mmol) and tetrahydrofuran (30 ml) was added dropwise n-butyllithium (1.57M n-hexane solution, 3.1 ml, 4.9 mmol) at −78° C. (external temperature). Then, the reaction mixture was stirred at the same temperature for 30 minutes. To the mixture was added dropwise triisopropyl borate (1.2 ml, 5.4 mmol) at −78° C. (external temperature). Then, the reaction mixture was stirred at 0° C. (external temperature) for 20 minutes. To the mixture was added potassium hydrogen fluoride (2.3 g, 29 mmol) at 0° C. (external temperature). Then, water (8 ml) was added dropwise to the reaction mixture at the same temperature. After the reaction mixture was raised to room temperature, the solvent was distilled off under reduced pressure. To the resulting residue were added acetone (100 ml) and methanol (5 ml), the mixture was heated, allowed to cool at around 40° C. (internal temperature), and filtrated. The solvent was distilled off from the filtrate under reduced pressure, and the residue was washed with diethyl ether:heptane=1:5, decanted, and dried under reduced pressure to obtain the title compound (140 mg, 0.56 mmol, 12%).

$^1$H-NMR Spectrum (CD$_3$OD) δ (ppm): 1.50-1.52 (2H, m), 1.62-1.68 (4H, m), 2.64 (4H, brs), 2.69 (2H, t, J=6.0 Hz), 2.80 (2H, q, J=5.6 Hz), 3.55 (2H, t, J=6.0 Hz).

Example 9A

Synthesis of potassium [(2-morpholin-4-ylethoxy)methyl]trifluoroborate

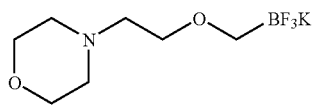

(9A-1) 4-(2-Tributylstannylmethoxyethyl)morpholine

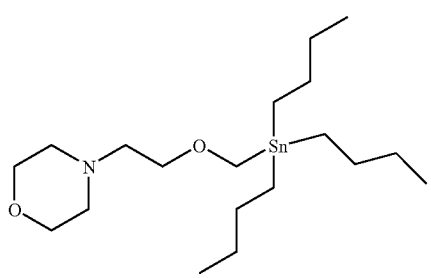

To a mixture of sodium hydride (72%, 230 mg, 7.0 mmol) and tetrahydrofuran (20 ml) was added N-(2-hydroxyethyl)morpholine (843 μl, 6.96 mmol) at room temperature. Then, the reaction mixture was stirred at 45° C. (external temperature) for 20 minutes. To the reaction mixture was added tributyl-iodomethyl-tin (2.0 g, 4.64 mmol) at 0° C. (external temperature). Then, the mixture was stirred at 45° C. for 30 minutes. After the reaction mixture was cooled to room temperature, ethyl acetate and water were added, and the organic layer was separated. The organic layer was washed with an aqueous saturated sodium chloride solution, and dried with anhydrous sodium sulfate. After the solvent was distilled off under reduced pressure, the residue was purified by silica gel column chromatography (NH silica gel, heptane:ethyl acetate=9:1) to obtain the title compound (1.7 g, 4.0 mmol, 85%).

$^1$H-NMR Spectrum (CDCl$_3$) δ (ppm): 0.81-0.97 (15H, m), 1.25-1.34 (6H, m), 1.46-1.54 (6H, m), 2.49-2.51 (4H, m), 2.55 (2H, t, J=5.6 Hz), 3.47 (2H, t, J=5.6 Hz), 3.70-3.74 (6H, m).

(9A-2) Potassium [(2-morpholin-4-ylethoxy)methyl]trifluoroborate

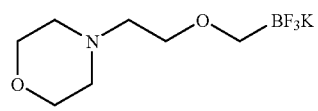

To a mixture of 4-(2-tributylstannylmethoxyethyl)morpholine (1.7 g, 4.0 mmol) and tetrahydrofuran (20 ml) was added dropwise n-butyllithium (1.52M n-hexane solution, 2.6 ml, 4.0 mmol) at −78° C. (external temperature), and the reaction mixture was stirred at the same temperature for 30 minutes. To the mixture was added dropwise triisopropyl borate (1.1 ml, 4.8 mmol) at −78° C. (external temperature), and the reaction mixture was stirred at 0° C. (external temperature) for 20 minutes. To the mixture was added potassium hydrogen fluoride (1.3 g, 16 mmol) at 0° C. (external temperature). Then, water (20 ml) was added dropwise to the reaction mixture at the same temperature. The reaction mixture was raised to room temperature, and the solvent was distilled off under reduced pressure. To the residue were added acetone (100 ml) and methanol (5 ml), followed by filtration. The solvent was distilled off from the filtrate under reduced pressure, and the residue was washed with diethyl ether to obtain the title compound (150 mg, 0.60 mmol, 15%).

$^1$H-NMR Spectrum (DMSO-d$_6$) δ (ppm): 2.35-2.39 (6H, m), 2.47 (2H, q, J=5.6 Hz), 3.26-3.31 (2H, m), 3.53-3.57 (4H, m).

Example 10A

Synthesis of potassium trifluoro[(3-morpholin-4-ylpropoxy)methyl]borate

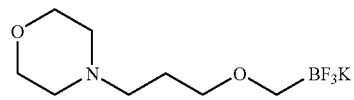

(1A-1) 4-{3-[(tributylstannyl)methoxy]propyl}morpholine

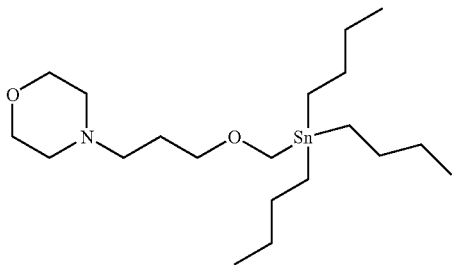

To a mixture of sodium hydride (60%, 278 mg, 6.96 mmol) and tetrahydrofuran (20 ml) was added N-(3-hydroxypropyl) morpholine (963 μl, 6.96 mmol) at room temperature. Then, the reaction mixture was stirred at 45° C. (external temperature) for 10 minutes. To the reaction mixture was added tributyl-iodomethyl-tin (2.0 g, 4.64 mmol) at 0° C. (external temperature). Then, the mixture was stirred at 45° C. for 1 hour. The reaction mixture was cooled at room temperature, diluted with ethyl acetate, washed sequentially with water and an aqueous saturated sodium chloride solution, and dried with anhydrous sodium sulfate. The solvent was distilled off under reduced pressure, and the residue was purified by silica gel column chromatography (NH silica gel, heptane:ethyl acetate=9:1) to obtain the title compound (2.08 g, 6.96 mmol, 100%).

$^1$H-NMR Spectrum (CDCl$_3$) δ (ppm): 0.81-0.97 (15H, m), 1.26-1.35 (6H, m), 1.42-1.54 (6H, m), 1.75 (2H, br s), 2.46 (6H, br s), 3.36 (2H, t, J=6.2 Hz), 3.70 (2H, t, J=7.0 Hz), 3.64 (4H, br s).

(10A-2) Potassium trifluoro[(3-morpholin-4-ylpropoxy)methyl]borate

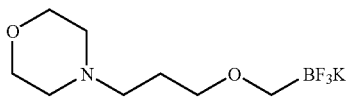

To a solution of 4-{3-[(tributylstannylmethoxy)propyl]}morpholine (2.08 g, 6.96 mmol) in tetrahydrofuran (100 ml) was added n-butyllithium (2.67 M, 1.74 ml, 4.64 mmol) at −78° C. (external temperature), and the mixture was stirred at the same temperature for 1 hour. Then, to the reaction mixture was added triisopropyl borate (1.29 ml, 5.56 mmol) at the same temperature. After the reaction mixture was stirred at 0° for 80 minutes, to the reaction mixture were added potassium hydrogen fluoride (1.45 g, 18.5 mmol) and water (50 ml) at the same temperature. Then, the reaction mixture was stirred at the same temperature. The solvent was distilled off under reduced pressure, and the residue was washed with ether. To the resulting residue were added acetone (100 ml) and methanol (5 ml), followed by filtration. The solvent was distilled off from the filtrate under reduced pressure. The residue was washed with ether to obtain the title compound (720 mg, 2.71 mmol, 59%).

$^1$H-NMR Spectrum (DMSO-d$_6$) δ (ppm): 1.53-1.60 (2H, m), 2.23-2.27 (2H, m), 2.31 (4H, m), 2.43 (2H, q, J=5.6 Hz), 3.18 (2H, t, J=6.4 Hz), 3.55 (4H, t, J=4.8 Hz).

Example 11A

Synthesis of potassium (1-methyl-piperidin-4-yloxy)methyl trifluoroborate

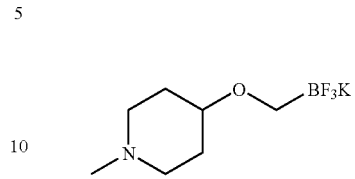

(11A-1) 1-Methyl-4-tributylstannylmethoxypiperidine

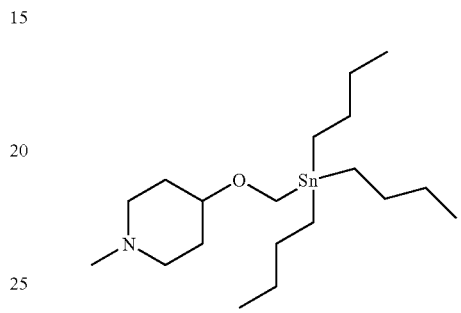

To a solution of 4-hydroxy-1-methylpiperidine (802 mg, 6.96 mmol) in tetrahydrofuran (20 ml) was added sodium hydride (50%, 334 mg, 6.96 mmol) at room temperature, and the mixture was stirred at room temperature for 35 minutes. To the reaction mixture were added a solution of tributyl-iodomethyl-tin (2.00 g, 4.64 mmol) in tetrahydrofuran (5 ml), and N,N-dimethylformamide (10 ml) at room temperature, and the mixture was stirred at room temperature for 7 hours and 50 minutes. To the reaction mixture was added water under ice-cooling, followed by extraction with ethyl acetate. The organic layer was washed sequentially with water and an aqueous saturated sodium chloride solution, and dried over anhydrous magnesium sulfate. After the solvent was distilled off under reduced pressure, the residue was purified by NH silica gel column chromatography (heptane:ethyl acetate=100:1 to 20:1) to obtain the title compound (1.42 g, 3.39 mmol, 73%).

$^1$H-NMR Spectrum (CDCl$_3$) δ (ppm): 0.87-0.91 (15H, m), 1.26-1.35 (6H, m), 1.47-1.55 (6H, m), 1.62 (2H, brs), 1.83 (2H, brs), 2.14 (2H, brs), 2.25 (3H, s), 2.60 (2H, brs), 3.07 (1H, brs), 3.69 (2H, t, J=7.9 Hz).

(11A-2) Potassium (1-methyl-piperidin-4-yloxy)methyl trifluoroborate

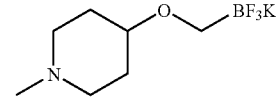

To a solution of 1-methyl-4-tributylstannylmethoxypiperidine (1.42 g, 3.39 mmol) in tetrahydrofuran (60 ml) was added n-butyllithium (1.59 M, 2.14 ml, 3.39 mmol) at −78° C. under the nitrogen atmosphere, followed by stirring at −78° C. for 30 minutes. To the reaction mixture was added triisopropyl borate (863 μl, 3.74 mmol) at −78° C. under the nitrogen atmosphere, followed by stirring at 0° C. for 20 minutes. Then, to the reaction mixture were added potassium hydrogen fluoride (1.06 g, 13.6 mmol) and water (10 ml) at 0° C., followed by stirring at room temperature for 10 minutes. After the solvent was distilled off from the reaction mixture under reduced pressure, acetone (30 ml) was added to the residue, followed by heating. After allowed to cool to around 40° C. (internal temperature), the resultant was filtered using Celite. After the solvent was distilled off from the filtrate under reduced pressure, the residue was washed with heptane to obtain the title compound (95 mg, 0.40 mmol, 12%).

$^1$H-NMR Spectrum (DMSO-$d_6$) δ (ppm): 1.25-1.34 (2H, m), 1.74-1.78 (2H, m), 1.90-1.95 (2H, m), 2.13 (3H, s), 2.45 (2H, q, J=5.5 Hz), 2.60-2.64 (2H, m), 2.88-2.93 (1H, m).

Example 12A

Synthesis of tetrabutylammonium methoxymethyl trifluoroborate

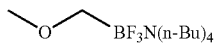

To a solution of potassium methoxymethyl trifluoroborate (500 mg, 3.29 mmol), described in Example 2A, in a mixture of methylene chloride (10 ml) and water (10 ml) was added tetrabutylammonium hydroxide (2.37 ml, 40% aqueous solution, 3.62 mmol) at room temperature, followed by stirring at room temperature for a few minutes. The mixed solution was extracted with methylene chloride, the resulting organic layer was dried over anhydrous magnesium sulfate, and the solvent was distilled off under reduced pressure to obtain the title compound (933 mg, 2.61 mmol, 80%).

$^1$H-NMR Spectrum (DMSO-$d_6$) δ (ppm): 0.918 (12H, t, J=7.5 Hz), 1.24-1.34 (8H, m), 1.51-1.59 (8H, m), 2.39 (2H, q, J=5.2 Hz), 3.04 (3H, s), 3.12-3.16 (8H, m).

(Example 13A)

Synthesis of potassium {[2-(1-methylpiperazin-4-yl)ethoxy]methyl}trifluoroborate

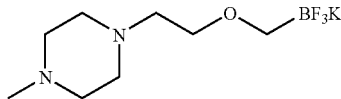

(13A-1) 1-Methyl-4-(2-tributylstannylmethoxyethyl)piperazine

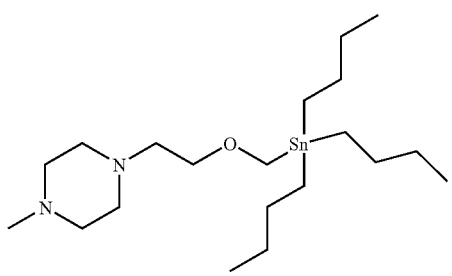

To a mixture of 1-(2-hydroxyethyl)-4-methylpiperazine (1.0 g, 6.9 mmol) and tetrahydrofuran (15 ml) was added sodium hydride (60%, 277 mg, 6.9 mmol) at 0° C. (external temperature), and the reaction mixture was stirred at room temperature for 30 minutes. Then, to the reaction mixture was added dropwise a mixture of tributyl-iodomethyl-tin (2.0 g, 4.6 mmol) and N,N-dimethylformamide (15 ml) at 0° C. (external temperature). Then, the reaction mixture was stirred at room temperature for 1.5 hours. To the reaction mixture were added water and ethyl acetate, and the organic layer was separated. The organic layer was washed with water and an aqueous saturated sodium chloride solution, and dried over anhydrous magnesium sulfate. The solvent was distilled off under reduced pressure. The residue was purified by silica gel column chromatography (heptane:ethyl acetate=10:1, NH silica gel) to obtain the title compound (1.9 g, 4.2 mmol, 92%).

$^1$H-NMR Spectrum (CDCl$_3$) δ (ppm): 0.89 (15H, t, J=7.6 Hz), 1.25-1.34 (6H, m), 1.46-1.54 (6H, m), 2.28 (3H, s), 2.46 (8H, brs), 2.56 (2H, t, J=5.6 Hz), 3.47 (2H, t, J=5.6 Hz), 3.73 (2H, s).

(13A-2) Potassium {[2-(1-methylpiperazin-4-yl)ethoxy]methyl} trifluoroborate

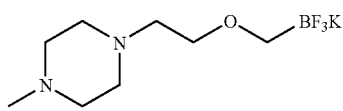

To a solution of 1-methyl-4-(2-tributylstannylmethoxyethyl)piperazine (400 mg, 0.90 mmol) and triisopropyl borate (0.32 ml, 1.4 mmol) in tetrahydrofuran (50 ml) was added dropwise n-butyllithium (1.6M n-hexane solution, 0.57 ml, 0.90 mmol) at −78° C. (external temperature). Then, the reaction mixture was stirred at the same temperature for 30 minutes. To the mixture was added potassium hydrogen fluoride (530 mg, 6.7 mmol) at −78° C. (external temperature). Then, the reaction mixture was raised to room temperature. After water (25 ml) was added dropwise to the reaction mixture at the same temperature, and the reaction mixture was stirred at the same temperature for 10 minutes, the solvent was distilled off under reduced pressure. To the resulting residue were added acetone (100 ml) and methanol (5 ml). The resultant was heated, then, allowed to cool to around 40° C. (internal temperature), followed by filtration. The solvent was distilled off from the filtrate under reduced pressure, and the residue was washed with diethyl ether-heptane (1:5) to obtain the title compound (4 mg, 0.015 mmol, 1.4%).

$^1$H-NMR Spectrum (CD$_3$OD) δ (ppm): 2.49 (3H, s), 2.80-2.84 (4H, m), 2.83 (2H, q, J=5.6), 3.10 (2H, t, J=5.2 Hz), 3.09-3.20 (4H, m), 3.62 (2H, t, J=5.2 Hz).

Example 14A

Synthesis of potassium 4-(dimethylamino)butoxymethyl trifluoroborate

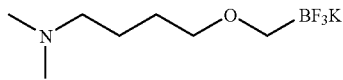

(14A-1) Dimethyl-(4-tributylstannylmethoxybutyl)amine

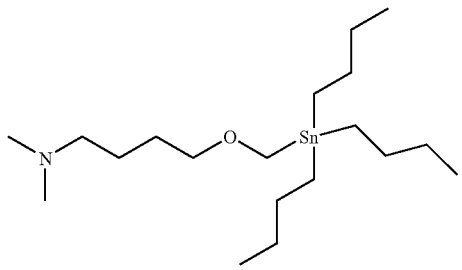

To a mixture of sodium hydride (72%, 232 mg, 7.0 mmol) and tetrahydrofuran (20 ml) was added 4-(dimethylamino)-1-butanol (0.82 g, 7.0 mmol) at 0° C. (external temperature), and the reaction mixture was stirred at 45° C. for 20 minutes. Then, the reaction mixture was cooled at 0° C. (external temperature). To the reaction mixture was added dropwise a mixture of tributyl-iodomethyl-tin (2.0 g, 4.6 mmol) and N,N-dimethylformamide (20 ml) at the same temperature. Then, the reaction mixture was stirred at 45° C. for 30 minutes. The reaction mixture was brought to room temperature, water and ethyl acetate were added to the reaction mixture, and the organic layer was separated. The organic layer was washed with water and an aqueous saturated sodium chloride solution, and the solvent was distilled off under reduced pressure. The residue was purified by silica gel column chromatography (heptane:ethylacetate=20:1, NH silica gel) to obtain the title compound (1.4 g, 3.3 mmol, 70%).

$^1$H-NMR Spectrum (CDCl$_3$) δ (ppm): 0.81-0.97 (15H, m), 1.26-1.35 (6H, m), 1.47-1.55 (10H, m), 2.21 (6H, s), 2.24-2.28 (2H, m), 3.30-3.33 (2H, m), 3.71 (2H, t, J=6.8 Hz).

(14A-2) Potassium 4-(dimethylamino)butoxymethyl trifluoroborate

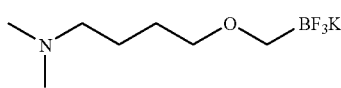

To a mixture of dimethyl-(4-tributylstannylmethoxybutyl)amine (500 mg, 1.2 mmol) and tetrahydrofuran (12 ml) was added triisopropyl borate (0.41 ml, 1.8 mmol) at −78° C. (external temperature). Then, to the reaction mixture was added dropwise n-butyllithium (1.5M n-hexane solution, 0.76 ml, 1.2 mmol) at the same temperature. After the reaction mixture was stirred at 0° C. (external temperature) for 20 minutes, potassium hydrogen fluoride (650 mg, 8.3 mmol) was added at the same temperature. Water (10 ml) was added dropwise at the same temperature to the mixture. Then, the reaction mixture was stirred at room temperature for 10 minutes. After the solvent was distilled off under reduced pressure, to the resulting residue were added acetone (100 ml) and methanol (5 ml), followed by filtration. The solvent was distilled off from the filtrate under reduced pressure, and the residue was washed with diethylether to obtain the title compound (55 mg, 0.23 mmol, 20%).

$^1$H-NMR Spectrum (CD$_3$OD) δ (ppm): 1.75-1.81 (2H, m), 1.85-1.91 (2H, m), 2.83 (6H, s), 2.87 (2H, q, J=5.6), 3.07 (2H, t, J=5.9 Hz), 3.44 (2H, t, J=5.4 Hz).

Example 15A

Synthesis of potassium {2-[cyclohexyl(methyl)amino]ethoxy}methyl trifluoroborate

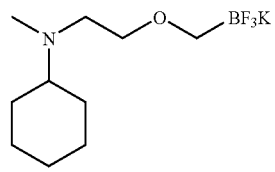

(15A-1) 2-[Cyclohexyl(methyl)amino]ethanol

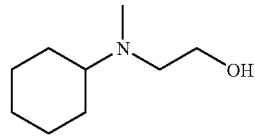

To a mixture of N-cyclohexylethanolamine (2.1 g, 14.7 mmol) and tetrahydrofuran (70 ml) were added iodomethane (1.1 ml, 17.6 mmol) and triethylamine (2.26 ml, 16.2 mmol) at room temperature, and the reaction mixture was stirred for 1 hour under heating refluxing. The reaction mixture was cooled at room temperature (external temperature). To the mixture was added water to stop the reaction. To the reaction mixture was added ethyl acetate, and the organic layer was separated. The organic layer was washed with water and an aqueous saturated sodium chloride solution, and the solvent was distilled off under reduced pressure. The residue was purified by silica gel chromatography (ethyl acetate, NH silica gel) to obtain the title compound (790.7 mg, 5.0 mmol, 34%).

$^1$H-NMR Spectrum (CDCl$_3$) δ (ppm): 1.03-1.12 (1H, m), 1.17-1.28 (4H, m), 1.61-1.65 (1H, m), 1.72-1.84 (4H, m), 2.24 (3H, s), 2.32-2.43 (1H, m), 2.59 (2H, t, J=5.6 Hz), 3.50 (2H, t, J=5.5 Hz).

(15A-2) N-Methyl-N-{2-[(tributylstannyl)methoxy]ethyl}cyclohexaneamine

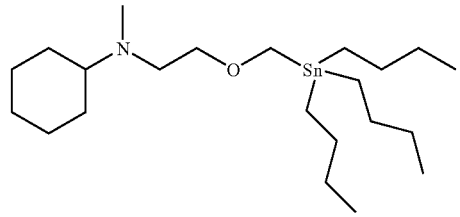

To a mixture of sodium hydride (50%, 241 mg, 5.0 mmol) and tetrahydrofuran (20 ml) was added 2-[cyclohexyl(methyl)amino]ethanol (791 mg, 5.0 mmol) at 0° C. (external temperature). Then, the reaction mixture was stirred at 60° C. for 30 minutes. After the reaction mixture was cooled at 0° C. (external temperature), to the reaction mixture was added dropwise a solution of tributyl-iodomethyl-tin (2.2 g, 5.0 mmol) in tetrahydrofuran (5 ml), and the reaction mixture was stirred at 60° C. for 1 hour. After the reaction mixture was cooled at room temperature (external temperature), water was added to stop the reaction. Ethyl acetate was added to the reaction mixture, and the organic layer was separated. After the organic layer was washed with water, an aqueous saturated sodium chloride solution, and then, the solvent was distilled off under reduced pressure. The residue was purified by silica gel chromatography (heptane:ethyl acetate=20:1, NH silica gel) to obtain the title compound (790.7 mg, 4.3 mmol, 85%).

¹H-NMR Spectrum (CDCl₃) δ (ppm): 0.87-0.91 (15H, m), 1.01-1.12 (1H, m), 1.16-1.24 (4H, m), 1.25-1.34 (6H, m), 1.46-1.54 (6H, m), 1.56-1.66 (1H, m), 1.76-1.82 (4H, m), 2.29 (3H, s), 2.32-2.40 (1H. m), 2.61 (2H, t, J=6.4 Hz), 3.40 (2H, t, J=6.4), 3.74 (2H, t, J=6.4 Hz).

(15A-3) Potassium {2-[cyclohexyl(methyl)amino]ethoxy}methyl trifluoroborate

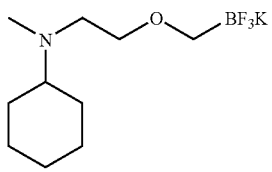

To a mixture of N-methyl-N-{2-[(tributylstannyl)methoxy]ethyl}cyclohexaneamine (500 mg, 1.1 mmol), triisopropyl borate (281 μl, 1.1 mmol) and tetrahydrofuran (40 ml) was added n-butyllithium (754 μl, 1.2 mmol) at −78° C. (external temperature), and the reaction mixture was raised to 0° C. (external temperature), and stirred for 30 minutes. Then, to the reaction mixture was added potassium hydrogen fluoride (511 mg, 6.54 mmol). To the reaction mixture was added dropwise water (20 ml) at the same temperature. The reaction mixture was raised to room temperature, and stirred for 1 hour, and the solvent was distilled off under reduced pressure. After to the resulting residue was added acetone-methanol (10:1) (100 ml), the resultant was heated, allowed to cool at around 40° C. (internal temperature), and filtered. The solvent was distilled off from the filtrate under reduced pressure, and the residue was washed using hexane to obtain the title compound (22.2 mg, 0.08 mmol, 7%).

¹H-NMR Spectrum (CD₃OD) δ (ppm): 1.20-1.40 (5H, m), 1.66-1.70 (1H, m), 1.86-1.94 (4H, m), 2.82 (2H, q, J=5.6 Hz), 2.90 (1H, br s), 2.95-3.07 (2H, m), 3.34 (3H, s), 3.58 (2H, t, J=5.6 Hz).

Example 16A

Synthesis of (2-methylpropoxy)methyl boronic acid

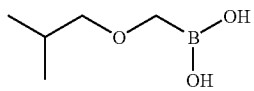

(16A-1) Tributyl-(2-methylpropoxy)methyl-tin

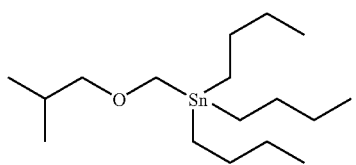

To a mixture of sodium hydride (66%, 250 mg, 7.0 mmol) and tetrahydrofuran (20 ml) were added 2-methylpropanol (0.69 ml, 7.4 mmol) and N,N-dimethylformamide (20 ml) at 0° C. (external temperature). Then, the reaction mixture was stirred at room temperature for 1 hour. To the reaction mixture was added dropwise tributyl-iodomethyl-tin (2.0 g, 4.6 mmol) at 0° C. (external temperature). Then, the reaction mixture was stirred at room temperature for 5 hours and a half. To the reaction mixture were added heptane and water, and the organic layer was separated. The organic layer was washed with an aqueous saturated sodium chloride solution, and the solvent was distilled off under reduced pressure. The residue was purified by silica gel column chromatography (heptane:ethyl acetate=20:1) to obtain the title compound (1.7 g, 4.4 mmol, 95%).

¹H-NMR Spectrum (CDCl₃) δ (ppm): 0.86-0.91 (21H, m), 1.26-1.35 (6H, m), 1.47-1.54 (6H, m), 1.78-1.88 (1H, m), 3.07 (2H, d, J=6.6 Hz), 3.71 (2H, t, J=6.6 Hz).

(16A-2) (2-Methylpropoxy)methyl boronic acid

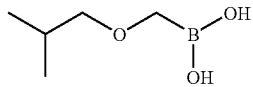

To a solution of tributyl-(2-methylpropoxy)methyl-tin (1.00 g, 2.65 mmol) in tetrahydrofuran (20 ml) was added dropwise n-butyllithium (1.54M n-hexane solution, 1.72 ml, 2.65 mmol) at −78° C. (external temperature) under the nitrogen atmosphere, and the reaction mixture was stirred at the same temperature for 35 minutes. Then, to the reaction mixture was added triisopropyl borate (1.10 ml, 4.74 mmol) at −78° C. (external temperature) under the nitrogen atmosphere, and the reaction mixture was stirred at room temperature for 50 minutes. To the reaction mixture was added a 1N aqueous sodium hydroxide solution at room temperature. The resultant was extracted three times, and the resulting aqueous layer was washed with diethyl ether. Then, to the resulting aqueous layer was added 5N aqueous hydrochloric acid solution to make the solution acidic, followed by extraction with diethyl ether three times. The resulting organic layer was washed with an aqueous saturated sodium chloride solution, dried over anhydrous magnesium sulfate, and filtered. The solvent was distilled off from the filtrate to obtain the title compound (101 mg, 0.765 mmol, 29%).

¹H-NMR Spectrum (CDCl₃) δ (ppm): 0.892 (6H, d, J=6.4 Hz), 1.80-1.90 (1H, m), 3.19 (2H, d, J=6.4 Hz), 3.21 (2H, s), 4.80 (2H, s).

Example B-1

1-Methoxymethyl-4-nitrobenzene

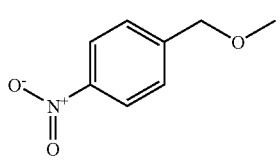

To a mixture of 4-nitrophenyl trifluoromethanesulfonate (30 mg, 0.11 mmol) and 1,4-dioxane (3 ml) were added water (0.3 ml), cesium carbonate (0.11 g, 0.34 mmol), potassium methoxymethyl trifluoroborate (17 mg, 0.11 mmol), palladium (II) acetate (1.3 mg, 0.0056 mmol) and tri-o-tolylphosphine (8.5 mg, 0.028 mmol). Then, the reaction mixture was stirred at 95° C. (external temperature) for 4 hours. After the reaction mixture was cooled at room temperature, water and heptane were added to the mixture, and the organic layer was separated. The organic layer was filtered, and the solvent was distilled off under reduced pressure. The residue was purified by NH-silica gel column chromatography (heptane:ethyl acetate=10:1) to obtain the title compound (13 mg, 0.078 mmol, 68%).

$^1$H-NMR Spectrum (CDCl$_3$) δ (ppm): 3.45 (3H, s), 4.56 (2H, s), 7.50 (2H, d, J=9.0 Hz), 8.21 (2H, d, J=8.8 Hz).

Example B-2

1-Methoxy-2-methoxymethyl-benzene

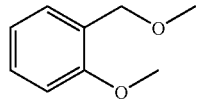

To a mixture of 2-bromoanisole (50 mg, 0.27 mmol) and 1,4-dioxane (2 ml) were added water (0.2 ml), cesium carbonate (0.26 g, 0.80 mmol), potassium methoxymethyl trifluoroborate (81 mg, 0.53 mmol), palladium (II) acetate (3.0 mg, 0.013 mmol) and 2-dicyclohexylphosphino-2',6'-dimethoxybiphenyl (11 mg, 0.027 mmol). Then, the reaction mixture was stirred at 100° C. (external temperature) overnight. After the reaction mixture was allowed to cool at room temperature, water and butane were added to the mixture, and the resultant was filtered using celite.

The organic layer was separated, and the organic layer was washed with an aqueous saturated sodium chloride solution. The organic layer was separated, and the solvent was distilled off under reduced pressure. The residue was purified by NH-silica gel column chromatography (heptane) to obtain the title compound (27 mg, 0.18 mmol, 66%).

$^1$H-NMR Spectrum (CDCl$_3$) δ (ppm): 3.42 (3H, s), 3.84 (3H, s), 4.51 (2H, s), 6.87-6.89 (1H, m), 6.96 (1H, td, J=7.4, 1.1 Hz), 7.25-7.29 (1H, m), 7.34-7.36 (1H, m).

Example B-3

1-t-Butoxymethyl-3-methoxybenzene

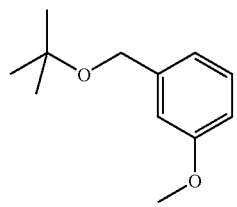

To a mixture of 3-bromoanisole (30 mg, 0.16 mmol) and 1,4-dioxane (2 ml) were added water (0.2 ml), cesium carbonate (0.26 g, 0.80 mmol), potassium t-butoxymethyl trifluoroborate (62 mg, 0.32 mmol), palladium (II) acetate (3.6 mg, 0.016 mmol) and 2-dicyclohexylphosphino-2',6'-dimethoxybiphenyl (13 mg, 0.032 mmol). Then, the reaction mixture was stirred at 100° C. (external temperature) overnight. After the reaction mixture was cooled at room temperature, water and heptane were added to the mixture, and the resultant was filtered using Celite. The separated organic layer was washed with an aqueous saturated sodium chloride solution. The organic layer was separated, and the solvent was distilled off under reduced pressure. The residue was purified by silica gel column chromatography (heptane:ethyl acetate=40:1) to obtain the title compound (26 mg, 0.13 mmol, 83%).

$^1$H-NMR Spectrum (CDCl$_3$) δ (ppm): 1.29 (9H, s), 3.81 (3H, s), 4.43 (2H, s), 6.79 (1H, dd, J=2.5, 8.2 Hz), 6.92-6.93 (2H, m), 7.24 (1H, t, J=8.2 Hz).

Example B-4

2-(2,4-Dimethylbenzyloxy)ethyl methyl ether

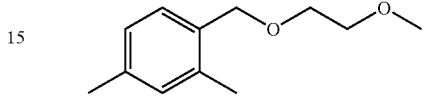

To a mixture of 4-bromo-m-xylene (30 mg, 0.16 mmol, containing 2-bromo-m-xylene) and 1,4-dioxane (2 ml) were added water (0.2 ml), cesium carbonate (0.16 mg, 0.49 mmol), potassium (2-methoxyethoxymethyl) trifluoroborate (64 mg 0.32 mmol), palladium (II) acetate (3.6 mg, 0.016 mmol) and 2-dicyclohexylphosphino-2',6'-dimethoxybiphenyl (13 mg, 0.032 mmol). Then, the reaction mixture was stirred at 100° C. (external temperature) for 12 hours. After the reaction mixture was allowed to cool at room temperature, to the reaction mixture was added water and hexane. The organic layer was washed with an aqueous saturated sodium chloride solution, and the organic layer was separated. After the organic layer was dried with anhydrous sodium sulfate, the solvent was distilled off under reduced pressure. The residue was purified by thin layer chromatography (hexane 100%) to obtain the title compound (32 mg, 0.16 mmol, 71%) as a mixture of 2-(2,6-dimethylbenzyloxy)ethyl methyl ether derived from 2-bromo-m-xylene contained in a raw material.

$^1$H-NMR Spectrum (CDCl$_3$) δ (ppm): 7.19 (1H, d, J=7.2 Hz), 7.00-6.95 (2H, m), 4.53 (2H, s), 3.61-3.53 (4H, m), 3.39 (3H, s), 2.31 (3H, s), 2.30 (3H, s).

Example B-5

4-Cyclopropylmethoxymethyl-biphenyl

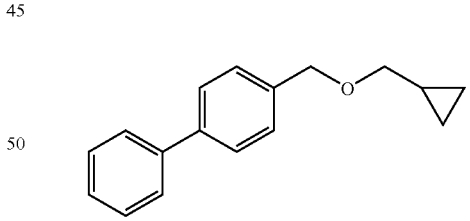

To a mixture of 4-chlorobiphenyl (50 mg, 265 μmol) and 1,4-dioxane (2 ml) were added water (0.2 ml), cesium carbonate (259 mg, 795 μmol), potassium cyclopropylmethoxymethyl trifluoroborate (102 mg, 530 mol), palladium (II) acetate (5.95 mg, 27 μmol) and 2-dicycrohexylphospino-2',6'-dimethoxybiphenyl (21.8 mg, 53.1 μmol). Then, the reaction mixture was stirred at 100° C. (external temperature) for 7 hours and 30 minutes. After the reaction mixture was cooled at room temperature, water and heptane were added to the mixture, followed by filtration using Celite. The separated organic layer was washed with an aqueous saturated sodium chloride solution. The organic layer was separated, and the solvent was distilled off under reduced pressure. The residue was purified by silica gel column chromatography (heptane: ethyl acetate=30:1) to obtain the title compound (57 mg, 239 μmol, 90%).

$^1$H-NMR Spectrum (CDCl$_3$) δ (ppm): 0.23 (2H, ddd, J=4.4 Hz, 6.0 Hz, 9.2 Hz), 0.53-0.58 (2H, m), 1.09-1.16 (1H, m), 3.35 (2H, d, J=6.8 Hz), 4.58 (2H, s), 7.32-7.36 (1H, m), 7.40-7.46 (4H, m), 7.56-7.60 (4H, m).

Example B-6

2-[(4-Butylbenzyl)oxy]-N,N-dimethylethaneamine

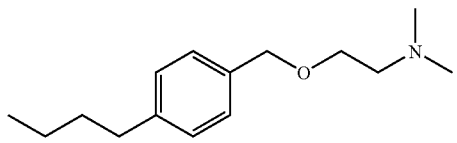

To a mixture of 1-bromo-4-butylbenzene (50 mg, 0.24 mmol) and 1,4-dioxane (1.5 ml) were added water (0.15 ml), cesium carbonate (0.23 g, 0.71 mmol), potassium {[2-(dimethylamino)ethoxy]methoxy}trifluorobrate (108 mg, 0.47 mmol), palladium (II) acetate (5.3 mg, 0.024 mmol) and 2-dicyclohexylphosphino-2',6'-dimethoxybiphenyl (19 mg, 0.047 mmol). Then, the reaction mixture was stirred at 100° C. (external temperature) for 10 hours. After the reaction mixture was cooled at room temperature, ethyl acetate and water were added to the mixture. The separated organic layer was washed with an aqueous saturated sodium chloride solution, and the organic layer was separated. After the organic layer was dried over anhydrous sodium sulfate, the solvent was distilled off under reduced pressure. The residue was purified with silica gel column chromatography (heptane: ethyl acetate=6:1, NH silica gel) to obtain the title compound (14 mg, 0.058 mmol, 25%).

$^1$H-NMR Spectrum (CDCl$_3$) δ (ppm): 0.92 (3H, t, J=7.2 Hz), 1.30-1.39 (2H, m), 1.55-1.62 (2H, m), 2.27 (6H, s), 2.53 (2H, t, J=5.8 Hz), 2.60 (2H, t, J=7.8 Hz), 3.54 (2H, t, J=5.8 Hz), 4.50 (2H, s), 7.15 (2H, d, J=8.0 Hz), 7.25 (2H, d, J=8.0 Hz).

Example B-7

2-(Biphenyl-4-ylmethoxy)ethanol

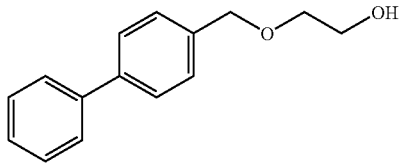

To a mixture of 4-chlorobiphenyl (15 mg, 79.5 μmol) and 1,4-dioxane (1.5 ml) were added water (0.15 ml), cesium carbonate (117 mg, 358 μmol), sodium (2-hydroxyethoxy) methyl trifluoroborate (19.7 mg, 119 mol), palladium (II) acetate (5.37 mg, 23.9 μmol) and 2-dicyclohexylphosphino-2',6'-dimethoxybiphenyl (19.6 mg, 47.7 μmol). Then, the reaction mixture was stirred at 100° C. (external temperature) for 13 hours. After the reaction mixture was cooled at room temperature, water and dichloromethane were added to the mixture, followed by filtration using Celite. The separated organic layer was washed with an aqueous saturated sodium chloride solution. The organic layer was separated, and the solvent was distilled off under reduced pressure. The residue was purified by silica gel column chromatography (heptane: ethyl acetate=1:1 NH silica gel) to obtain the title compound (6.8 mg, 30 μmol, 38%).

$^1$H-NMR Spectrum (DMSO-d$_6$) δ (ppm): 3.48-3.50 (2H, m), 3.54-3.58 (2H, m), 4.54 (2H, s), 4.66 (1H, t, J=5.6 Hz), 7.34-7.39 (1H, m), 7.42-7.49 (4H, m), 7.64-7.68 (4H, m).

Example B-8

3-(2-Morpholin-4-yl-ethoxymethyl)-quinoline

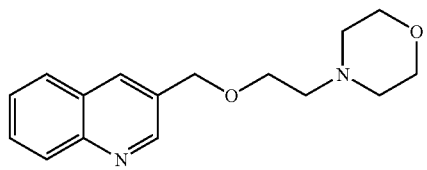

To a mixture of 3-bromoquinoline (80 mg, 0.39 mmol) and 1,4-dioxane (4 ml) were added water (0.4 ml), cesium carbonate (564 mg, 1.7 mmol), [(2-morpholin-4-ylethoxy)-methyl]trifluoroborate (145 mg, 0.58 mmol), palladium (II) acetate (8.6 mg, 0.04 mmol) and 2,2'-bis(diphenylphosphino) 1,1'-binaphthyl (48 mg 0.08 mmol). Then, the reaction mixture was stirred at 100° C. (external temperature) for 15 hours. After the reaction mixture was cooled at room temperature, water and ethyl acetate were added to the mixture, followed by filtration using Celite. The separated organic layer was washed with an aqueous saturated sodium chloride solution. The organic layer was separated, and the solvent was distilled off under reduced pressure. The residue was purified by NH silica gel column chromatography (heptane:ethyl acetate=1: 2) to obtain the title compound (3.2 mg, 0.01 mmol, 3.1%).

$^1$H-NMR Spectrum (CDCl$_3$) δ (ppm): 2.51 (4H, t, J=4.4 Hz), 2.65 (2H, t, J=5.6 Hz), 3.67 (2H, t, J=5.6 Hz), 3.73 (4H, t, J=4.4 Hz), 4.75 (2H, s), 7.54-7.58 (1H, m), 7.70-7.74 (1H, m), 7.81-7.83 (1H, m), 8.10-8.12 (2H, m), 8.90-8.91 (1H, m).

Example B-9

1-(4-Methoxymethyl-phenyl)ethanone

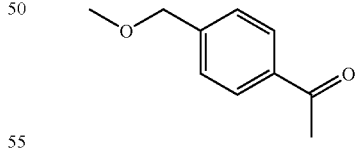

To a mixture of 4'-bromoacetophenone (300 mg, 1.51 mmol) and 1,4-dioxane (4 ml) were added water (0.4 ml), cesium carbonate (1.48 g, 4.54 mmol), potassium methoxymethyl trifluoroborate (459 mg, 3.02 mmol) and 1',1'-bis (diphenylphosphino)ferrocenedichloropalladium (II) (110 mg, 0.151 mmol). Then, the reaction mixture was stirred at 100° C. (external temperature) for 7 hours. After the reaction mixture was cooled at room temperature, water and methylene chloride were added to the mixture, followed by filtration using Celite. The separated organic layer was washed with an aqueous saturated sodium chloride solution. The organic

Example B-10

Methyl 4-methoxymethyl-benzoate

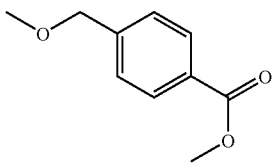

To a mixture of methyl 4-bromobenzoate (50 mg, 0.233 mmol) and 1,4-dioxane (1 ml) were added water (0.1 ml), cesium carbonate (228 mg, 0.7 mmol), potassium methoxymethyl trifluoroborate (71 mg, 0.467 mmol) and 1',1'-bis(diphenylphosphino)ferrocenedichloropalladium (II) (17 mg, 0.023 mmol). Then, the reaction mixture was stirred at 100° C. (external temperature) for 4.5 hours. After the reaction mixture was cooled at room temperature, water and methylene chloride were added to the mixture, followed by filtration using celite. The separated organic layer was washed with an aqueous saturated sodium chloride solution. The organic layer was separated, and the solvent was distilled off under reduced pressure. The residue was purified by silica gel column chromatography (heptane:ethylacetate=10:1) to obtain the title compound (13.9 mg, 33%).

$^1$H-NMR Spectrum (CDCl$_3$) δ (ppm): 3.41 (3H, s), 3.91 (3H, s), 4.51 (2H, s), 7.39 (2H, d, J=8.4 Hz), 7.99-8.03 (2H, m).

Example B-11

4-Isobutoxymethyl-biphenyl

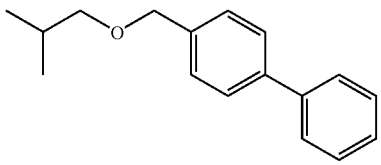

To a solution of 4-chlorobiphenyl (25 mg, 0.13 mmol) in 1,4-dioxane (1 ml) and water (100 μl) were added (2-methylpropoxy)methyl boronic acid (35 mg, 0.27 mmol), palladium (II) acetate (3.0 mg, 0.013 mmol), 2-dicyclohexylphosphino-2',6'-dimethoxybiphenyl (11 mg, 0.027 mmol), and cesium carbonate (130 mg, 0.40 mmol) at room temperature. The reaction mixture was stirred at 100° C. for 7 hours and 50 minutes under the nitrogen atmosphere. After the reaction mixture was cooled at room temperature, water was added to the mixture, followed by filtration using Celite. After the filtrate was extracted with ethyl acetate, the organic layer was washed with water and an aqueous saturated sodium chloride solution, dried over anhydrous magnesium sulfate, and filtered. The solvent was distilled off from the filtrate under reduced pressure. The residue was purified by silica gel column chromatography (heptane:ethylacetate=30:1) to obtain the title compound (9.0 mg, 0.037 mmol, 28%) as a colorless oil.

$^1$H-NMR Spectrum (CDCl$_3$) δ (ppm): 0.948 (6H, d, J=6.8 Hz), 1.90-1.97 (1H, m), 3.27 (2H, d, J=6.6 Hz), 4.55 (2H, s), 7.32-7.36 (1H, m), 7.41-7.46 (4H, m), 7.56-7.61 (4H, m).

Example B-12

Biphenyl-4-yl-methanol

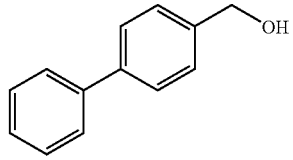

To a mixture of 4-chlorobiphenyl (23 mg, 0.12 mmol), 1,4-dioxane (2 ml) and water (200 μl) were added potassium acetoxymethyl trifluoroborate (44 mg, 0.24 mmol), palladium (II) acetate (14 mg, 0.061 mmol), 2-dicyclohexylphosphino-2',6'-dimethoxybiphenyl (50 mg, 0.12 mmol), and potassium phosphate (170 mg, 0.73 mmol) at room temperature. The reaction mixture was heated to reflux overnight under the nitrogen atmosphere. After the reaction mixture was cooled at room temperature, water and ethyl acetate were added to the mixture. After the organic layer was washed with an aqueous saturated sodium chloride solution, the solvent was distilled off under reduced pressure. The residue was purified by silica gel column chromatography (heptane:ethyl acetate=2:1) to obtain the title compound (18 mg, 0.098 mmol, 80%).

$^1$H-NMR Spectrum (CDCl$_3$) δ (ppm): 4.75 (2H, s), 7.33-7.37 (1H, m), 7.43-7.46 (4H, m), 7.59-7.61 (4H, m).

Example B-13

2,2-Dimethyl-propionic acid pyridin-3-ylmethyl ester

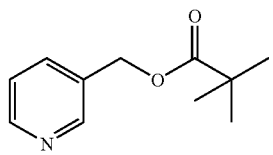

To a solution of 3-chloropyridine (50 mg, 0.44 mmol) in 1,4-dioxane (2 ml) and water (200 μl) were added sodium [(2,2-dimethyl)propionyloxy]methyl trifluoroborate (181 mg, 0.88 mmol), palladium (II) acetate (9.9 mg, 0.044 mmol), 2-dicyclohexylphosphino-2',6'-dimethoxybiphenyl (36 mg, 0.088 mmol), and potassium phosphate (405 mg, 1.76 mmol) at room temperature. The reaction mixture was stirred at 100° C. for 14 hours and 15 minutes under the nitrogen atmosphere. After the reaction mixture was cooled at room temperature, water was added to the mixture, followed by filtration using Celite. After the filtrate was extracted with ethyl acetate, the organic layer was washed with an aqueous saturated sodium chloride solution, dried over anhydrous magnesium sulfate, and filtered. The solvent was distilled off from the filtrate under reduced pressure. The residue was purified by NH silica gel column chromatography (heptane:ethyl acetate=2:1) to obtain the title compound (10 mg, 0.052 mmol, 12%).

$^1$H-NMR Spectrum (CDCl$_3$) δ (ppm): 1.23 (9H, s), 5.13 (2H, s), 7.28-7.32 (1H, m), 7.66-7.69 (1H, m), 8.58 (1H, dd, J=1.7 Hz, 4.8 Hz), 8.62 (1H, d, J=1.7 Hz).

Example B-14

Pyridin-3-yl-methanol

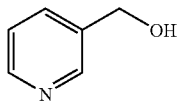

As a side product of (Example B-13), the title compound (6.8 mg, 0.062 mmol, 14%) was obtained.

$^1$H-NMR Spectrum (CDCl$_3$) δ (ppm): 4.73 (2H, s), 7.28-7.31 (1H, m), 7.72-7.75 (1H, m), 8.49 (1H, dd, J=1.7 Hz, 4.9 Hz), 8.55 (1H, d, J=2.0 Hz).

Example B-15

(R)-3-(Biphenyl-4-ylmethoxy)-pyrrolidine-1-carboxylic acid t-butyl ester

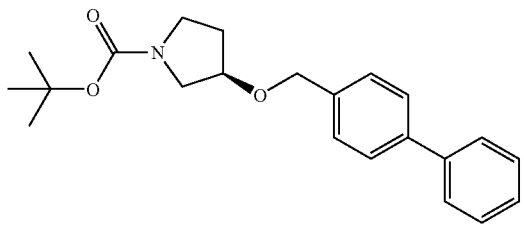

To a mixture of 4-bromobiphenyl (15 mg, 64.3 μmol) and 1,4-dioxane (1.5 ml) were added water (0.15 ml), cesium carbonate (94.3 mg, 289 μmol), sodium [[[[3R]-1-t-butoxycarbonyl]pyrrolidin-3-yl]oxy]methyl(trifluoro)borate (28.1 mg, 96.5 μmol), palladium (II) acetate (4.33 mg, 19.3 μmol) and 1,4-bis(diphenylphosphino)butane (8.23 mg, 19.3 μmol). Then, the reaction mixture was stirred at 100° C. (external temperature) for 7 hours. After the reaction mixture was cooled at room temperature, water and dichloromethane were added to the mixture, followed by filtration using Celite. The organic layer was washed with an aqueous saturated sodium chloride solution, and the solvent was distilled off under reduced pressure. The residue was purified by NH silica gel column chromatography (heptane:ethylacetate=6:1), and further purified by preparative thin layer chromatography (heptane:ethyl acetate=4:1 NH silica gel) to obtain the title compound (4.1 mg, 11.6 μmol, 18%).

$^1$H-NMR Spectrum (CD$_3$OD) δ (ppm): 1.46 (9H, s), 1.90-2.05 (1H, m), 2.05-2.15 (1H, m), 3.37-3.55 (4H, m), 4.21 (1H, br s), 4.55-4.61 (2H, m), 7.32-7.34 (1H, m), 7.40-7.44 (4H, m), 7.59-7.62 (4H, m).

Example B-16

2-Methoxymethyl-5-nitro-thiophene

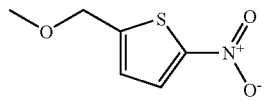

A mixture of potassium methoxymethyl trifluoroborate (33 mg, 0.22 mmol), 2-bromo-5-nitrothiophene (30 mg, 0.14 mmol), 1,4-dioxane (1.5 ml), water (0.15 ml), cesium carbonate (235 mg, 0.72 mmol), palladium (II) acetate (3.2 mg, 0.014 mmol), and 2,2'-bis(diphenylphosphino)-1,1'-binaphthyl (9.0 mg, 0.014 mmol) was stirred at 100° C. (external temperature) for 6 hours. After the reaction mixture was cooled at room temperature, water and ethyl acetate were added to the mixture, followed by filtration using Celite. The organic layer was washed with an aqueous saturated sodium chloride solution, and the solvent was distilled off under reduced pressure. The residue was purified by NH silica gel column chromatography (heptane:ethyl acetate=3:1) to obtain the title compound (2.7 mg, 0.016 mmol, 11%).

$^1$H-NMR Spectrum (CD$_3$OD) δ (ppm): 3.43 (3H, s), 4.65 (2H, d, J=0.9 Hz), 7.04 (1H, dt, J=4.2, 0.9 Hz), 7.89 (1H, d, J=4.2 Hz).

Example C1

Synthesis of 2-(chloromethyl)-4,4,5,5-tetramethyl-1,3,2-dioxaborane

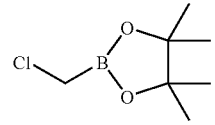

To a mixture of triisopropyl borate (15 ml, 65 mmol), chloroiodomethane (13 g, 72 mmol) and tetrahydrofuran (78 ml) was added dropwise n-butyllithium (1.6M n-hexane solution, 41 ml, 65 mmol) at −78° C. (external temperature) over 20 minutes. Then, the mixture was stirred at room temperature for 2.5 hours. After the reaction mixture was cooled at 0° C. (external temperature), to the mixture was added dropwise a 4N hydrochloric acid-ethyl acetate solution in order to neutralize at the same temperature. To the reaction mixture was added pinacol (7.7 g, 65 mmol) at the same temperature, and then, the reaction mixture was stirred at room temperature for 40 minutes. After the solvent was distilled off under reduced pressure, the resulting residue was distilled under reduced pressure (63-70° C., 11 mmHg) to obtain the title compound (9.2 g, 52 mmol, 81%).

$^1$H-NMR Spectrum (CDCl$_3$) δ (ppm): 1.30 (12H, s), 2.97 (2H, s).

Example C2

Synthesis of 2-(bromomethyl)-4,4,5,5-tetramethyl-1,3,2-dioxaborolane

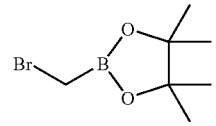

To a mixture of triisopropyl borate (20 g, 110 mmol), dibromomethane (8.6 ml, 120 mmol) and tetrahydrofuran (150 ml) was added dropwise n-butyllithium (2.6 M n-hexane solution, 39 ml, 100 mmol) at −78° C. (external temperature) over 1.5 hours. Then, the reaction mixture was stirred at the same temperature for 1.5 hours, and at room temperature for 2 hours. After the mixture was cooled at 0° C. (external temperature), to the reaction mixture was added methanesulfonic acid (6.5 ml, 100 mmol), and then, the reaction mixture was stirred at room temperature for 1 hour. After the mixture was cooled at 0° C. (external temperature), to the reaction mixture was added pinacol (12 g, 100 mmol), and then, the reaction mixture was stirred at room temperature for 1 hour. After the solvent was distilled off under reduced pressure, the resulting residue was distilled under reduced pressure (74-76° C., 8 mmHg) to obtain the title compound (16 g, 72 mmol, 68%).

$^1$H-NMR Spectrum (CDCl$_3$) δ (ppm): 1.29 (12H, s), 2.59 (2H, s).

Example C3

Synthesis of sodium cyclopropylmethoxymethyl trifluoroborate

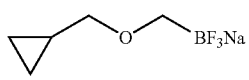

To a mixture of sodium hydride (66%, 430 mg, 12 mmol) and tetrahydrofuran (20 ml) was added cyclopropylmethanol (1.2 ml, 15 mmol) at 0° C. (external temperature). Then, the reaction mixture was stirred at room temperature for 30 minutes. To the reaction mixture was added 2-(bromomethyl)-4,4,5,5-tetramethyl-1,3,2-dioxaborolane (2.0 g, 9.1 mmol) at 0° C. (external temperature), and then, the mixture was stirred at room temperature for 1 hour, and stirred at 45° C. (external temperature) for 4 hours. After the reaction mixture was cooled at 0° C. (external temperature), sodium hydrogen fluoride (2.2 g, 36 mmol) was added to the mixture, and then, to the reaction mixture was added dropwise water (15 ml) at the same temperature. After the reaction mixture was raised to room temperature, the solvent was distilled off under reduced pressure. To the resulting residue were added acetone (100 ml) and methanol (1 ml), and the mixture was heated, then, allowed to cool to around 40° C. (internal temperature), and filtered. The solvent was distilled off from the filtrate under reduced pressure, and the residue was washed with ethyl acetate to obtain the title compound (1.2 g, 6.8 mmol, 75%).

$^1$H-NMR Spectrum (DMSO-d$_6$) δ (ppm): 0.05-0.09 (2H, m), 0.35-0.40 (2H, m), 0.86-0.96 (1H, m), 2.46 (2H, q, J=5.6 Hz), 3.00 (2H, d, J=6.8 Hz).

Example C4

Synthesis of Potassium Butoxymethyl Trifluoroborate

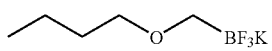

To a mixture of 1-butanol (1.6 ml, 17 mmol) and tetrahydrofuran (40 ml) was added potassium bis(trimethylsilyl)amide (0.5M toluene solution, 36 ml, 18 mmol) at 0° C. (external temperature). Then, the reaction mixture was stirred at room temperature for 30 minutes. To the reaction mixture was added 2-(chloromethyl)-4,4,5,5-tetramethyl-1,3,2-dioxabororane (1.0 g, 5.7 mmol) and potassium iodide (94 mg, 0.57 mmol) at room temperature. Then, the mixture was stirred at 60° C. (external temperature) for 4 hours. After the reaction mixture was cooled at 0° C. (external temperature), potassium hydrogen fluoride (2.7 g, 34 mmol) was added to the mixture, and then, to the reaction mixture was added dropwise water (20 ml) at the same temperature. After the reaction mixture was raised to room temperature, the solvent was distilled off under reduced pressure. To the resulting residue was added acetone (100 ml), and the mixture was heated, and then, cooled at room temperature. The mixture was filtered to obtain the filtrate and the solid. The resulting filtrate was subjected to distillation of the solvent under reduced pressure, and the residue was washed with ethyl acetate to obtain the title compound (220 mg, 1.1 mmol, 20%). Further, to the resulting solid were added acetone (95 ml) and methanol (5 ml), and the mixture was stirred, and filtered. Then, the solvent was distilled off from the filtrate under reduced pressure to obtain the title compound (260 mg, 1.3 mmol, 24%).

$^1$H-NMR Spectrum (DMSO-d$_6$) δ (ppm): 0.86 (3H, t, J=7.4 Hz), 1.24-1.30 (2H, m), 1.38-1.43 (2H, m), 2.42-2.48 (2H, m), 3.17 (2H, t, J=6.8 Hz).

Example C5

Synthesis of sodium [[[[3R]-1-t-butoxycarbonyl]pyrrolidin-3-yl]oxy]methyl(trifluoro)borate

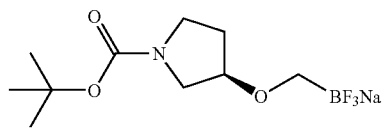

To a mixture of sodium hydride (50%, 478 mg, 10 mmol) and tetrahydrofuran (20 ml) was added N-t-butoxycarbonyl-(R)-3-hydroxypyrrolidine (1.7 g, 9.1 mmol) at 0° C. (external temperature), and the reaction mixture was stirred at 50° C. for 1 hour. To the reaction mixture was added 2-(bromomethyl)-4,4,5,5-tetramethyl-1,3,2-dioxabororane (2.0 g, 9.1 mmol) at 0° C. (external temperature), and the mixture was stirred at 60° C. for 1.5 hours. The reaction mixture was cooled at room temperature, and filtered, and the solvent was distilled off from the filtrate under reduced pressure. To a mixture of the residue and methanol (30 ml) was added sodium hydrogen fluoride (1.68 g, 27.2 mmol) at 0° C. (external temperature). Then, to the reaction mixture was added dropwise water (20 ml). After the reaction mixture was stirred at room temperature for 1 hour, the solvent was distilled off under reduced pressure. To the resulting residue was added acetone (100 ml), and the mixture was heated, allowed to cool to around 40° C. (internal temperature), and filtered. After the solvent was distilled off from the filtrate under reduced pressure, to the resulting residue was added tetrahydrofuran, hexane was added until two layers were formed, and the supernatant was removed. Further, using methanol and hexane, the similar procedure was repeated four times, and the solvent was distilled off from the residue under reduced pressure to obtain the title compound (911.4 mg, 3.1 mmol, 35%).

$^1$H-NMR Spectrum (DMSO-$d_6$) δ (ppm): 1.40 (9H, s), 1.70-1.80 (1H, m), 1.80-1.90 (1H, m), 2.41-2.48 (2H, m), 3.11-3.27 (4H, m), 3.74 (1H, br s).

Example C6

Synthesis of Sodium Isopropoxymethyl Trifluoroborate

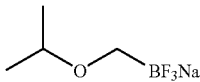

To a mixture of sodium hydride (61%, 232 mg, 5.89 mmol) and tetrahydrofuran (14 ml) was added 2-propanol (0.55 ml, 7.25 mmol) at 0° C. (external temperature). Then, the reaction mixture was stirred at room temperature for 30 minutes. To the reaction mixture was added 2-(bromomethyl)-4,4,5,5-tetramethyl-1,3,2-dioxabororane (1.0 g, 4.53 mmol) at 0° C. (external temperature), and the mixture was stirred at room temperature for 1 hour, and at 45° C. (external temperature) for 2 hours. After the reaction mixture was cooled at 0° C. (external temperature), sodium hydrogen fluoride (1.12 g, 18.1 mmol) was added to the mixture, and then, to the reaction mixture was added dropwise water (8 ml) at the same temperature. After the reaction mixture was raised to room temperature, the solvent was distilled off under reduced pressure. To the resulting residue were added acetone (50 ml) and methanol (0.5 ml), followed by filtration. The solvent was distilled off from the filtrate under reduced pressure, and the residue was washed with diethyl ether to obtain the title compound (585 mg, 3.56 mmol, 79%).

$^1$H-NMR Spectrum (DMSO-$d_6$) δ (ppm): 0.97 (6H, d, J=6.0 Hz), 2.40 (2H, q, J=5.6 Hz), 3.14-3.24 (1H, m).

Example C7

Synthesis of sodium tetrahydrofuran-2-ylmethoxymethyl trifluoroborate

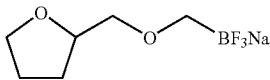

To a mixture of sodium hydride (61%, 232 mg, 5.89 mmol) and tetrahydrofuran (14 ml) was added tetrahydrofurfuryl alcohol (0.70 ml, 7.25 mmol) at 0° C. (external temperature), and the reaction mixture was stirred at room temperature for 2 hours. To the reaction mixture was added 2-(bromomethyl)-4,4,5,5-tetramethyl-1,3,2-dioxabororane (1.0 g, 4.53 mmol) at 0° C. (external temperature). The mixture was stirred at room temperature for 1 hour, and then, at 45° C. (external temperature) for 2 hours. After the reaction mixture was cooled at 0° C. (external temperature), sodium hydrogen fluoride (1.12 g, 18.1 mmol) was added to the mixture, and to the reaction mixture was added dropwise water (8 ml) at the same temperature. After the reaction mixture was raised to room temperature, the solvent was distilled off under reduced pressure. To the resulting residue were added acetone (50 ml) and methanol (0.5 ml), followed by filtration. The solvent was distilled off from the filtrate, and the residue was washed with diethyl ether to obtain the title compound (379 mg, 1.84 mmol, 41%).

$^1$H-NMR Spectrum (DMSO-$d_6$) δ (ppm): 1.40-1.49 (1H, m), 1.72-1.86 (3H, m), 2.44 (2H, q, J=5.6 Hz), 3.11-3.18 (2H, m), 3.55 (1H, dd, J=7.2, 14.2 Hz), 3.67 (1H, dd, J=6.4, 14.2 Hz) 3.79-3.86 (1H, m).

Example C8

Synthesis of sodium tetrahydropyran-4-yloxy-methyl trifluoroborate

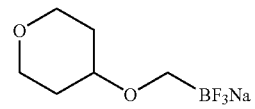

To a mixture of tetrahydro-4H-pyran-4-ol (500 mg, 4.9 mmol) and tetrahydrofuran (7 ml) was added sodium hydride (66%, 135 mg, 3.7 mmol) at 0° C. (external temperature), and the reaction mixture was stirred at room temperature for 15 minutes. Then, to the reaction mixture was added 2-(bromomethyl)-4,4,5,5-tetramethyl-1,3,2-dioxabororane (630 mg, 2.9 mmol) at 0° C. (external temperature), and the mixture was stirred at 45° C. (external temperature) for 4 hours. After the reaction mixture was cooled at 0° C. (external temperature), sodium hydrogen fluoride (707 mg, 11 mmol) was added to the mixture, and then, to the reaction mixture was added dropwise water (3 ml) at the same temperature. After the reaction mixture was raised to room temperature, the solvent was distilled off under reduced pressure. To the resulting residue were added acetone (100 ml) and methanol (1 ml), and the mixture was heated, allowed to cool to around 40° C. (internal temperature), and filtered. The solvent was distilled off from the filtrate under reduced pressure, and the residue was washed with diethyl ether to obtain the title compound (498 mg, 2.4 mmol, 85%).

$^1$H-NMR Spectrum (CD$_3$OD) δ (ppm): 1.46-1.53 (2H, m), 1.93-1.97 (2H, m), 2.81 (2H, q, J=5.6 Hz), 3.33-3.51 (1H, m), 3.37-3.43 (2H, m), 3.89-3.94 (2H, m).

Example C9

Synthesis of sodium 2-cyclohexyloxy-ethoxymethyl trifluoroborate

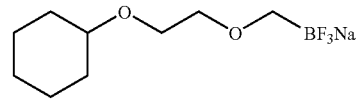

To a mixture of 2-(cyclohexyloxy)ethanol (521 mg, 3.6 mmol) and tetrahydrofuran (7 ml) was added sodium hydride (66%, 107 mg, 2.9 mmol) at 0° C. (external temperature), and the reaction mixture was stirred at room temperature for 15 minutes. Then, to the reaction mixture was added 2-(bromomethyl)-4,4,5,5-tetramethyl-1,3,2-dioxabororane (500 mg, 2.3 mmol) at 0° C. (external temperature), and the mixture was stirred at 45° C. (external temperature) for 4 hours. After the reaction mixture was cooled at 0° C. (external temperature), sodium hydrogen fluoride (560 mg, 9.0 mmol) was added to the mixture, and then, to the reaction mixture was added dropwise water (3 ml) at the same temperature. After the reaction mixture was raised to room temperature, the solvent was distilled off under reduced pressure. To the resulting residue were added acetone (100 ml) and methanol (1 ml), and the mixture was heated, allowed to cool to around 40° C.

(internal temperature), and filtered. The solvent was distilled off from the filtrated under reduced pressure, and the residue was washed with a mixed solution of diethyl ether:heptane=1:3 to obtain the title compound (162 mg, 0.65 mmol, 29%).

¹H-NMR Spectrum (CD₃OD) δ (ppm): 1.20-1.34 (5H, m), 1.54-1.57 (1H, m), 1.73-1.77 (2H, m), 1.93-1.96 (2H, m), 2.82 (2H, q, J=5.6 Hz), 3.23-3.33 (1H, m), 3.49-3.52 (2H, m), 3.59-3.61 (2H, m).

Example C10

Synthesis of sodium 3-methoxy-1-propoxymethyl trifluoroborate

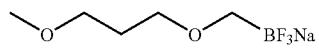

To a mixture of sodium hydride (60%, 236 mg, 5.9 mmol) and tetrahydrofuran (10 ml) was added 3-methoxy-1-propanol (0.73 ml, 7.3 mmol) at 0° C. (external temperature), and the reaction mixture was stirred at room temperature for 1 hour. To the reaction mixture was added 2-(bromomethyl)-4,4,5,5-tetramethyl-1,3,2-dioxabororane (1.0 g, 4.5 mmol) at 0° C. (external temperature), and the reaction mixture was stirred at 60° C. (external temperature) for 2.5 hours. After the reaction mixture was cooled at room temperature, insolubles in the reaction solution were removed by filtration. After the organic layer was cooled at 0° C. (external temperature), sodium hydrogen fluoride (1.12 g, 18.1 mmol) was added to the mixture, and then, to the reaction mixture was added dropwise water (7.5 ml) at the same temperature. After the reaction mixture was stirred at room temperature for 30 minutes, the solvent was distilled off under reduced pressure. To the resulting residue were added acetone (40 ml) and methanol (2 ml), followed by filtration. After the solvent was distilled off from the filtrate under reduced pressure, the residue was washed with heptane, followed by t-butyl methyl ether, to obtain the title compound (0.52 g, 2.7 mmol, 59%).

¹H-NMR Spectrum (DMSO-d₆) δ (ppm): 1.65 (2H, tt, J=6.4 and 6.4 Hz), 2.45 (2H, q, J=5.6 Hz), 3.20 (3H, s), 3.18-3.40 (4H, m).

Example C11

Synthesis of sodium (2-hydroxyethoxy)methyl trifluoroborate

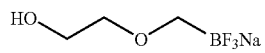

(C11-1) Sodium 2,2,3,3-tetramethyl-1,4,6,9-tetraoxa-5-boraspiro(4,5)decan-5-uide

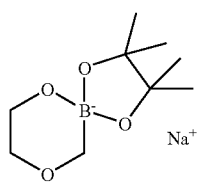

To a mixture of sodium hydride (50%, 478 mg, 10.0 mmol) and tetrahydrofuran (20 ml) was added a solution of ethylene glycol (562 mg, 9.1 mmol) in tetrahydrofuran at 0° C. (external temperature). Then, the reaction mixture was stirred for 30 minutes under heating refluxing. To the reaction mixture was added 2-(bromomethyl)-4,4,5,5-tetramethyl-1,3,2-dioxabororane (2.0 g, 9.1 mmol) at 0° C. (external temperature). Then, the mixture was stirred for 2 hours under heating refluxing. After the reaction mixture was cooled at 0° C. (external temperature), the precipitated solid was collected by filtration, to obtain the title compound (1.3 g) as a mixture with an inorganic salt.

¹H-NMR Spectrum (DMSO-d₆) δ (ppm): 0.85 (6H, s), 0.96 (6H, s), 2.63 (2H, br s), 3.17-3.19 (2H, m), 3.45-3.46 (2H, m).

(C11-2) Sodium (2-hydroxyethoxy)methyl trifluoroborate

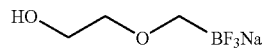

To a mixture of sodium 2,2,3,3-tetramethyl-1,4,6,9-tetraoxa-5-boraspiro(4,5)decan-5-uide (1.3 g) and methanol (30 ml) was added sodium hydrogen fluoride (800 mg, 12.9 mmol) at 0° C. (external temperature). Then, to the reaction mixture was added dropwise water (20 ml) at the same temperature. After the reaction mixture was stirred at room temperature for 1.5 hours, the solvent was distilled off under reduced pressure. To the resulting residue were added acetone (100 ml) and methanol (1 ml), and the mixture was heated, allowed to cool to around 40° C. (internal temperature), and filtered. After the solvent was distilled off from the filtrate under reduced pressure, the residue was washed with diethyl ether to obtain the title compound (188 mg, 1.2 mmol, 18%).

¹H-NMR Spectrum (CD₃OD-d₆) δ (ppm): 2.76-2.84 (2H, m), 3.44-3.47 (2H, m), 3.63-3.65 (2H, m).

Example C12

Synthesis of Potassium Acetoxymethyl Trifluoroborate

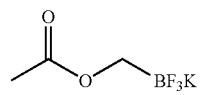

To a mixture of 2-(chloromethyl)-4,4,5,5-tetramethyl-1,3,2-dioxabororane (2.3 g, 13 mmol) and tetrahydrofuran (40 ml) were added potassium acetate (2.0 g, 20 mmol) and potassium iodide (66 mg, 0.40 mmol) at room temperature, followed by heating to reflux for 4 hours and 25 minutes. After the reaction mixture was cooled at 0° C. (external temperature), potassium hydrogen fluoride (5.2 g, 67 mmol) was added to the mixture, and then, to the reaction mixture was added dropwise water (25 ml) at the same temperature. After the reaction mixture was raised to room temperature, the solvent was distilled off under reduced pressure. The residue was washed with ethyl acetate. Then, to the residue was added acetone (100 ml) and the resultant was heated, allowed to cool to room temperature, and filtered. The solvent was distilled off from the filtrate under reduced pressure to obtain the title compound (1.3 g, 7.2 mmol, 56%).

$^1$H-NMR Spectrum (DMSO-$d_6$) δ (ppm): 1.88 (3H, s), 3.06 (2H, d, J=5.2 Hz).

Example C13

Synthesis of Sodium Formyloxymethyl Trifluoroborate

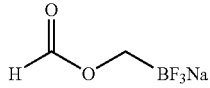

To a solution of 2-(bromomethyl)-4,4,5,5-tetramethyl-1,3,2-dioxabororane (1.0 g, 4.5 mmol) in tetrahydrofuran was added sodium formate (462 mg, 6.8 mmol) at room temperature, and the reaction mixture was heated to reflux for 1 hour and 40 minutes under the nitrogen atmosphere. To the reaction mixture was added acetonitrile (10 ml), and the reaction mixture was heated to reflux for 19 hours. After the reaction mixture was cooled at 0° C. (external temperature), to the reaction mixture was added sodium hydrogen fluoride (1.7 g, 27 mmol), and then, to the reaction mixture was added dropwise water (15 ml) at the same temperature. After the reaction mixture was raised to room temperature, the solvent was distilled off under reduced pressure. To the resulting residue was added acetone (25 ml), and the mixture was heated, allowed to cool at around 40° C. (internal temperature), and filtered. The solvent was distilled off from the filtrate under reduced pressure, and the residue was washed with ethyl acetate to obtain the title compound (90 mg, 0.60 mmol, 13%).

$^1$H-NMR Spectrum (DMSO-$d_6$) δ (ppm): 3.15 (2H, d, J=4.8 Hz), 8.07 (1H, s).

Example C14

Synthesis of Sodium [(cyclopentylcarbonyl)oxy]methyl trifluoroborate

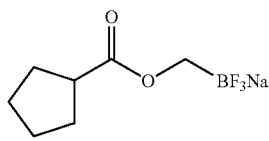

To a solution of cyclopentanecarboxylic acid (1.0 g, 8.8 mmol) in tetrahydrofuran (20 ml) was added a 5N aqueous sodium hydroxide solution (1.75 ml, 8.8 mmol) at room temperature. The reaction mixture was stirred for several minutes, and the solvent was distilled off under reduced pressure. To a mixture of the residue and tetrahydrofuran (20 ml) was added 2-(bromomethyl)-4,4,5,5-tetramethyl-1,3,2-dioxabororane (1.0 g, 4.5 mmol) at room temperature, and the reaction mixture was heated to reflux for 4 hours and 45 minutes under the nitrogen atmosphere. After the reaction mixture was cooled at 0° C. (external temperature), sodium hydrogen fluoride (1.4 g, 23 mmol) was added to the mixture, and then, to the reaction mixture was added dropwise water (5 ml) at the same temperature. After the reaction mixture was raised to room temperature, the solvent was distilled off under reduced pressure. To the resulting residue was added acetone (25 ml), the mixture was heated. Then, the reaction mixture was allowed to cool at around 40° C. (internal temperature), and filtered. After the solvent was distilled off from the filtrate under reduced pressure, the residue was washed with diethyl ether to obtain the title compound (837 mg, 3.8 mmol, 85%).

$^1$H-NMR Spectrum (DMSO-$d_6$) δ (ppm): 1.45-1.66 (6H, m), 1.70-1.76 (2H, m), 2.53-2.59 (1H, m), 3.04 (2H, q, J=5.6 Hz).

Example C15

Synthesis of sodium [(2,2-dimethyl)propionyloxy]methyl trifluoroborate

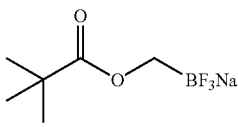

To a solution of pivalic acid (694 mg, 6.8 mmol) in tetrahydrofuran (20 ml) was added a 5N aqueous sodium hydroxide solution (1.36 ml, 6.8 mmol) at room temperature. The reaction mixture was stirred for a few minutes, and the solvent was distilled off under reduced pressure. To a mixture of the residue and tetrahydrofuran (20 ml) was added 2-(bromomethyl)-4,4,5,5-tetramethyl-1,3,2-dioxabororane (1.0 g, 4.5 mmol) at room temperature, and the reaction mixture was heated to reflux for 2 hours and 25 minutes under the nitrogen atmosphere. After the reaction mixture was cooled at 0° C. (external temperature), sodium hydrogen fluoride (1.4 g, 23 mmol) was added to the mixture, and then, to the reaction mixture was added dropwise water (10 ml) at the same temperature. After the reaction mixture was raised to room temperature, the solvent was distilled off under reduced pressure. To the resulting residue was added acetone (25 ml), and the mixture was heated, then, allowed to cool to around 40° C. (internal temperature), and filtered. The solvent was distilled off from the filtrate under reduced pressure, and the residue was washed with diethyl ether to obtain the title compound (895 mg, 4.3 mmol, 96%).

$^1$H-NMR Spectrum (DMSO-$d_6$) δ (ppm): 1.07 (9H, s), 3.07 (2H, q, J=5.3 Hz).

The invention claimed is:

1. A compound represented by following formula I:

(Formula I)

wherein M represents an alkali metal, $N(R^1)(R^2)(R^3)(R^4)$ or $P(R^1)(R^2)(R^3)(R^4)$ in which $R^1$, $R^2$, $R^3$ and $R^4$ each independently represents a $C_{1-6}$ alkyl group or a $C_{7-15}$ aralkyl group, provided that M forms a counterion with an anion in a molecule;

X represents a $C_{1-6}$ alkyl group optionally having 1 to 3 groups selected from a following group A, a $C_{3-8}$ cycloalkyl group optionally having 1 to 3 groups selected from a following group A, a 5- to 6-membered non-aromatic heterocyclic group optionally having 1 to 3 groups selected from a following group Z, or $R^5C$ (=O) in which $R^5$ represents a hydrogen atom, a $C_{1-6}$ alkyl group or a $C_{3-8}$ cycloalkyl group;

the group A represents an amino group optionally having a C$_{1-6}$ alkyl group or a C$_{3-8}$ cycloalkyl group, a hydroxy group, a C$_{1-6}$ alkyl group, a C$_{3-8}$ cycloalkyl group, a C$_{1-6}$ alkoxy group, a C$_{3-8}$ cycloalkoxy group, and 5- to 6-membered non-aromatic heterocyclic group optionally having 1 to 3 groups selected from the following group Z;

the group Z represents a C$_{1-6}$ alkyl group or a C$_{1-6}$ alkoxycarbonyl group;

m represents an integer of 0 or 1;

k represents an integer of 0 or 1.

2. A compound represented by following formula I-a:

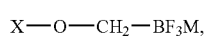

$$X-O-CH_2-BF_3M, \quad \text{(Formula I-a)}$$

wherein M represents an alkali metal, N(R$^1$)(R$^2$)(R$^3$)(R$^4$) or P(R$^1$)(R$^2$)(R$^3$)(R$^4$) in which R$^1$, R$^2$, R$^3$ and R$^4$ each independently represents a C$_{1-6}$ alkyl group or a C$_{7-15}$ aralkyl group, provided that M forms a counterion with an anion in a molecule;

X represents a C$_{1-6}$ alkyl group optionally having 1 to 3 groups selected from a following group A, a C$_{3-8}$ cycloalkyl group optionally having 1 to 3 groups selected from a following group A, a 5- to 6-membered non-aromatic heterocyclic group optionally having 1 to 3 groups selected from a following group Z, or R$^5$C(=O) in which R$^5$ represents a hydrogen atom, a C$_{1-6}$ alkyl group or a C$_{3-8}$ cycloalkyl group;

the group A represents an amino group optionally having a C$_{1-6}$ alkyl group or a C$_{3-8}$ cycloalkyl group, a hydroxy group, a C$_{1-6}$ alkyl group, a C$_{3-8}$ cycloalkyl group, a C$_{1-6}$ alkoxy group, a C$_{3-8}$ cycloalkoxy group, and 5- to 6-membered non-aromatic heterocyclic group optionally having 1 to 3 groups selected from a following group Z;

the group Z represents a C$_{1-6}$ alkyl group or a C$_{1-6}$ alkoxycarbonyl group.

3. The compound according to claim 1 or 2, wherein M is an alkali metal.

4. The compound according to claim 1 or 2, wherein M is potassium or sodium.

5. The compound according to claim 1, wherein the 5- to 6-membered non-aromatic heterocyclic group is a tetrahydrofuranyl group, a tetrahydropyranyl group, a piperidyl group, a pyrrolidinyl group or a morpholinyl group.

6. The compound according to claim 1, wherein X is a C$_{1-6}$ alkyl group optionally having 1 to 3 groups selected from a following group A1;

the group A1 represents an amino group optionally having a C$_{1-6}$ alkyl group or a C$_{3-8}$ cycloalkyl group, a hydroxy group, a C$_{1-6}$ alkyl group, a C$_{3-8}$ cycloalkyl group, a C$_{1-6}$ alkoxy group, a C$_{3-8}$ cycloalkoxy group, and a 5- to 6-membered non-aromatic heterocyclic group optionally having 1 to 3 groups selected from a following group Z1;

the group Z1 represents a C$_{1-6}$ alkyl group or a C$_{1-6}$ alkoxycarbonyl group.

7. A compound selected from a group consisting of potassium t-butoxymethyl trifluoroborate, potassium methoxymethyl trifluoroborate, potassium ethoxymethyl trifluoroborate, potassium (2-methoxyethoxymethyl) trifluoroborate, potassium cyclopropylmethoxymethyl trifluoroborate, potassium {[2-(dimethylamino)ethoxy]methyl} trifluoroborate, potassium cyclobutoxymethyl trifluoroborate, potassium 2-piperidin-1-ylethoxy -methyl trifluoroborate, potassium [(2-morpholine-4-ylethoxy)methyl]trifluoroborate, potassium trifluoro[(3-morpholin-4-ylpropoxy)methyl]borate, potassium (1-methyl-piperidin-4-yloxy)-methyl trifluoroborate, tetrabutylammonium methoxymethyl trifluoroborate, potassium {[2-(1-methylpiperazin-4-yl)ethoxy]methyl} trifluoroborate, potassium 4-(dimethylamino)butoxymethyl trifluoroborate, potassium {2-[cyclohexyl(methyl)amino]ethoxy}methyl trifluoroborate, (2-methylpropoxy)methyl boronic acid, sodium cyclopropylmethoxymethyl trifluoroborate, potassium butoxymethyl trifluoroborate, sodium [[[[3R]-1-t-butoxycarbonyl]pyrrolidin-3-yl]oxy]methyl(trifluoro)borate, sodium isopropoxymethyl trifluoroborate, sodium tetrahydrofuran-2-ylmethoxymethyl trifluoroborate, sodium tetrahydropyran-4-yloxy-methyl trifluoroborate, sodium 2-cyclohexyloxy-ethoxymethyl trifluoroborate, sodium 3-methoxy-1-propoxymethyl trifluoroborate, sodium (2-hydroxyethoxy)methyl trifluoroborate, potassium acetoxymethyl trifluoroborate, sodium formyloxymethyl trifluoroborate, sodium [(cyclopentylcarbonyl)oxy]methyl trifluoroborate, and sodium [(2,2-dimethyl)propionyloxy]methyl trifluoroborate.

* * * * *